(12) United States Patent
Saltzstein

(10) Patent No.: US 8,273,053 B2
(45) Date of Patent: Sep. 25, 2012

(54) PATIENT STATUS SENSOR

(75) Inventor: William E. Saltzstein, Woodinville, WA (US)

(73) Assignee: Pyng Medical Corp., Richmond (CA)

( * ) Notice: Subject to any disclaimer, the term of this patent is extended or adjusted under 35 U.S.C. 154(b) by 38 days.

(21) Appl. No.: 12/773,730

(22) Filed: May 4, 2010

(65) Prior Publication Data

US 2010/0286607 A1    Nov. 11, 2010

Related U.S. Application Data

(60) Provisional application No. 61/175,746, filed on May 5, 2009.

(51) Int. Cl.
*A61M 31/00* (2006.01)
(52) U.S. Cl. ...................................... 604/93.01
(58) Field of Classification Search .................. 600/301, 600/393; 604/93.01
See application file for complete search history.

(56) References Cited

U.S. PATENT DOCUMENTS

| | | |
|---|---|---|
| 3,677,261 A | 7/1972 | Day |
| 5,312,364 A | 5/1994 | Jacobs |
| 5,443,072 A | 8/1995 | Kagan et al. |
| 5,511,553 A * | 4/1996 | Segalowitz ............... 600/508 |
| 5,623,938 A | 4/1997 | Addiss |
| 5,634,468 A | 6/1997 | Platt et al. |
| 5,817,052 A | 10/1998 | Johnson et al. |
| 5,948,006 A | 9/1999 | Mann |
| 5,960,797 A | 10/1999 | Kramer et al. |
| 6,081,194 A | 6/2000 | Sanchez |
| 6,277,079 B1 | 8/2001 | Avicola et al. |
| 6,572,636 B1 | 6/2003 | Hagen et al. |
| 6,761,726 B1 | 7/2004 | Findlay et al. |
| 7,347,840 B2 | 3/2008 | Findlay et al. |
| 7,670,328 B2 | 3/2010 | Miller |
| 7,699,850 B2 | 4/2010 | Miller |
| 2001/0014439 A1 | 8/2001 | Meller et al. |

(Continued)

FOREIGN PATENT DOCUMENTS
WO    WO 2009/036334    3/2009

OTHER PUBLICATIONS

3M Red Dot Electrodes, Trusted Choices for Consistent Performance, Product Brochure, 2009.

(Continued)

*Primary Examiner* — Nicholas Lucchesi
*Assistant Examiner* — Melissa A Snyder
(74) *Attorney, Agent, or Firm* — Connolly Bove Lodge & Hutz LLP

(57) ABSTRACT

Embodiments of a patient status sensor can be applied to a patient or trauma victim to provide a quick visual and/or audible indication of the patient's vital signs (e.g., respiration, heart rate, or other vital signs). Certain embodiments are configured as an adhesive patch that includes electrodes for measuring heart rate (and respiration in some implementations), a processor configured to perform calculations for determining one or more vital signs using information from the electrodes, and audible or visual indicators to communicate information about vital signs or patient status to a medical attendant. Certain embodiments include an access opening for providing intraosseous delivery of fluids to bone marrow (e.g., through sternal or long bone) and can be integrated or used with an intraosseous delivery system. Certain embodiments include wired or wireless components to communicate vital signs or patient status to an external monitoring device.

40 Claims, 13 Drawing Sheets

U.S. PATENT DOCUMENTS

| | | | |
|---|---|---|---|
| 2005/0038348 | A1 | 2/2005 | Avicola et al. |
| 2005/0277841 | A1 | 12/2005 | Shennib |
| 2006/0030781 | A1 | 2/2006 | Shennib |
| 2006/0030782 | A1 | 2/2006 | Shennib |
| 2006/0264767 | A1 | 11/2006 | Shennib |
| 2007/0049945 | A1 | 3/2007 | Miller |
| 2007/0282181 | A1 | 12/2007 | Findlay et al. |
| 2008/0091090 | A1 | 4/2008 | Guillory et al. |
| 2008/0208136 | A1 | 8/2008 | Findlay et al. |
| 2008/0287859 | A1* | 11/2008 | Miller et al. .......... 604/21 |
| 2008/0319278 | A1 | 12/2008 | Omtveit et al. |
| 2009/0062670 | A1 | 3/2009 | Sterling et al. |

OTHER PUBLICATIONS

Aerotel Medical Systems Ltd., Heartline—Heart 2005A & Heart 2006—Single/Dual Lead Transtelephonic ECG Loop Event Recorder/Transmitter, downloaded Apr. 2010 from http://www.aerotel.com, in 2 pages.

Aerotel Medical Systems Ltd., Heartline—The Best of Tele-Cardiology, downloaded Apr. 2010 from http://www.aerotel.com, in 2 pages.

Afonso, V., "ECG QRS Detection," Chapter 12 in Biomedical Digital Signal Processing—C-Language Examples and Laboratory Experiments for the IBM PC edited by W. J. Tompkins, Prentice Hall, 1993, pp. 236-263.

Alive Technologies Pty Ltd, Mobile Cardiac Monitoring—Bluetooth ECG and Activity Monitor Product Brochure, downloaded Apr. 2010 from www.alivetec.com, in 1 page.

Baker, L. E., "Applications of the Impedance Technique to the Respiratory System," IEEE Engineering in Medicine and Biology Magazine, Mar. 1989, pp. 50-52.

Guidelines for Field Triage of Injured Patients: Recommendations of the National Expert Panel on Field Triage, Morbidity and Mortality Weekly Report, Centers for Disease Control and Prevention, Jan. 23, 2009, vol. 48, No. RR-1.

Christiaens et al., "3D Integration of Ultra-Thin Functional Devices Inside Standard Multilayer Flex Laminates," Abstract from Microelectronics and Packaging Conference, 2009 EMPC, Jun. 2009, in 1 page.

Eberle et al., "Health-Care Electronics—The Market, the Challenges, the Progress, Design," Abstract from Design, Automation & Test in Europe Conference & Exhibition, Apr. 2009, in 1 page.

Folke et al., "Critical Review of Non-Invasive Respiratory Monitoring in Medical Care," Medical & Biological Engineering & Computing, vol. 41, pp. 377-383, 2003.

Integrated Medical Devices, Inc., IMD Model 1200 Transtelephonic ECG Receiver, 2007.

Ke et al., "A Patch-type Wireless Physiological Monitoring Microsystems," Abstract from 9th International Conf. on e-Health Networking, Application and Services, Jun. 2007, in 1 page.

Montgomery et al., "Lifeguard—A Personal Physiological Monitor for Extreme Environments," available from http://lifeguard.stanford.edu/presentations/embc_lifeguard_paper_FINAL.pdf in Feb. 2010, in 4 pages.

Nonin Medical, Inc., Onyx II Model 9560 Pulse Oximetry, Fingertip, Product Brochure, 2008.

Pyng Medical Corp., "Chest is Best—FAST1 Sternal Line is the Quickest Route to the Heart," FAST1 Intraosseous Infusion System Brochure, Aug. 2008.

Pyng Medical Corp., FAST1 Intraosseous Infusion System Trainer's Manual, Aug. 2008, in 18 pages.

Pyng Medical Corp., FAST1 Intraosseous Infusion System, Selected Abstracts, downloaded from http://www.fast1sternal.com/about-io/technicalclinical/, Apr. 2010, in 7 pages.

Pyng Medical Corp., FASTx Sternal Intraosseous Device Product Brochure, Apr. 2010.

Pyng Medical Corp., K080865 510(k) Summary, dated Apr. 24, 2008, in 5 pages.

Raju, "Heart-Rate and EKG Monitor Using the MSP430FG439," Application Report SLAA280A—Oct. 2005—Revised Sep. 2007, Texas Instruments Incorporated, pp. 1-12.

Tompkins, W. J., "ECG Signal Characteristics," in Biomedical Digital Signal Processing—C-Language Examples and Laboratory Experiments for the IBM PC, Prentice Hall, 1993, p. 43.

Bradycardia, from Wikipedia, downloaded Jun. 21, 2010, in 5 pages.

Tachycardia, from Wikipedia, downloaded Jun. 21, 2010, in 6 pages.

Triage, from Wikipedia, downloaded Jun. 21, 2010, in 14 pages.

Vidacare, EZ-IO—Intraosseous Infusion System, EZ-IO Product System, downloaded Apr. 2010 from http://www.vidacare.com, in 4 pages.

Vidacare, EZ-IO—Intraosseous Infusion Systems Brochure, Product System for Military Use, downloaded Apr. 2010 from http://www.vidacare.com, in 4 pages.

Vidacare, EZ-IO Product Systems for Military Use Specifications Sheet, downloaded Apr. 2010 from http://www.vidacare.com, in 2 pages.

Welch Allyn, Directions for Use, Micropaq Monitor, Model 402 and Model 404, 2007, in 76 pages.

Welch Allyn, Propaq LT Vital Signs Monitor Quick Reference, 2005, in 1 page.

Yang et al., "Intelligent Electrode Design for Long-Term ECG Monitoring at Home: Prototype Design Using FPAA and FPGA," Abstract from 3rd International Conference on Pervasive Computing Technologies for Healthcare, Apr. 2009, in 1 page.

Yoo et al., "A Wearable ECG Acquisition System with Compact Planar-Fashionable Circuit Board-Based Shirt," IEEE Transactions on Information Technology in Biomedicine, vol. 13, No. 6, Nov. 2009, pp. 897-902.

International Search Report and Written Opinion of the International Searching Authority dated May 30, 2011 for corresponding International Application No. PCT/US2010/054336 dated Oct. 27, 2010; total pages 10.

\* cited by examiner

PATIENT STATUS SENSOR

CROSS-REFERENCE TO RELATED APPLICATIONS

This application claims the benefit under 35 U.S.C. §119(e) to U.S. Provisional Patent Application No. 61/175,746, filed May 5, 2009, titled "PATIENT STATUS SENSOR FOR INTRAOSSEOUS DRUG DELIVERY SYSTEM," which is hereby incorporated by reference herein in its entirety.

BACKGROUND

1. Field

The present disclosure relates to apparatus, methods, and systems for monitoring status of a patient.

2. Description of Related Art

Treatment of victims of traumatic injuries requires swift action. There are often many casualties, and each patient often requires the administration of large amounts of fluids, blood products and medications in the first few minutes to survive. On the battlefield and in traumatic crashes, access to traditional sites on patients for the insertion of intravenous lines may be difficult or even impossible due to damage to peripheral sites (e.g., arms, legs). The use of large veins such as the jugular is difficult and introduces a high rate of complicating issues in addition to the difficulty of safe mechanical fixation of the components involved. Other difficulties can occur.

Monitoring of patients in large-scale emergency medical situations such as mass transit accidents, terror attacks, or battlefields is often difficult due to the limitations on the numbers of medical personnel and equipment. There are often far too few devices to monitor all of the victims and even fewer personnel making it impossible for each patient to be continuously supervised. Speed in assessing and preparing patients can be important for introducing fluids and medication to the patient as well as setting up diagnostic and monitoring equipment. Complicated attachment of standard equipment and devices designed for hospital use such as, e.g., fluid lines and vital signs sensors may take too much time in these situations.

SUMMARY

In view of the aforementioned and other limitations, improvements in apparatus, systems, and methods for monitoring and treating patients, particularly trauma patients, are desirable. For example, certain embodiments provide an easy-to-use, disposable, single-use patient status sensor (e.g., a "patch" sensor) that can be applied to trauma patients (e.g., accident victims, victims of natural disasters, battlefield or terror casualties, ICU or emergency room patients, etc.). The patient status sensor can include visual or audible indicators that allow medical personnel to tell at a glance the condition or vital signs of the patient, e.g., the respiration rate and/or heart rate of the patient. Certain embodiments can be configured for use with intraosseous (IO) delivery systems that deliver fluids to bone marrow of the patient. Certain embodiments can include wired or wireless (e.g., radio frequency or frequency modulated audio signals) components to communicate vital signs or patient status information from the patient status sensor to external monitoring devices.

Certain embodiments of the patient status sensor, with or without IO infusion components, can be readily applied to a patient or trauma victim to provide a quick visual indication of the patient's vital signs (e.g., respiration and heart rate or other vital signs) and perform any calculations or processing for determining the vital signs on the patient status sensor itself (e.g., via a processor on the sensor). Certain such embodiments do not include components for wired and/or wireless communication of vital signs or other sensor data "off" the patient status sensor in order to provide an inexpensive, lightweight sensor that is less likely to fail in trauma situations. Other embodiments can include wired and/or wireless communication components.

Many vital signs are available with relatively large signal strength or convenient access in the chest and sternal area. Examples include, but are not limited to, ECG, respiration, blood pressure, core body temperature, glucose, pH, and blood oxygen. In some embodiments, an IO needle assembly can be used to insert a bone portal through a bone. One or more sensors (e.g., temperature, pressure) integrated with the bone portal provide direct access to the core body temperature as well as fluid pressures that are related to the patient's blood pressure. Access to blood and blood-borne fluids via the bone portal provide the capability, in some embodiments, to measure, for example, blood oxygen content, pH, and/or glucose. The system electronics of embodiments of the disclosed patient status sensor can be used to monitor output from such sensors and to use the sensor information, at least in part, to determine patient status. In some embodiments, other parametric sensors can be incorporated with the portal or the patient status sensor.

An embodiment of an intraosseous (IO) fluid delivery and patient status system is provided. The IO system comprises an IO infusion device configured to provide access to an IO space in a bone of a patient. The IO infusion device comprises a bone portal that comprises a fluid delivery channel. The bone portal has a proximal end and a distal end. The distal end is configured to be inserted into the bone. For example, the distal end of the bone portal can be configured to be inserted into the sternum or a long bone (e.g., tibia, humerus) of the patient. The IO infusion device further comprises a fluid delivery conduit configured to be coupled to the proximal end of the bone portal so as to provide fluid access to the fluid delivery channel of the bone portal. The IO system also comprises a patient status sensor configured to monitor at least one vital sign of the patient. The patient status sensor includes a flexible substrate that comprises an adhesive component configured to adhere the patient status sensor to the patient. The patient status sensor also includes a plurality of electrodes disposed in or on the substrate and configured to receive an electrical signal from the body of the patient and in response to provide a body signal. The patient status sensor also includes a visual indicator and a power source configured to be electrically connected to the visual indicator and a processor. The processor can be configured to (a) receive and process the body signal from the plurality of electrodes in order to determine a measurement of a vital sign, (b) determine patient status based at least in part on the measurement of the vital sign and one or more vital sign limits, and (c) output a patient status signal to the visual indicator. The visual indicator can be configured to output visual information indicative of the patient status.

An embodiment of a patient status sensor configured to monitor at least heart beat and respiration of a patient is provided. The patient status sensor comprises a flexible substrate that includes an adhesive layer configured to adhere the patient status sensor to the patient. The patient status sensor also comprises a visual indicator disposed in or on the substrate and a plurality of electrodes disposed in or on the substrate. The patient status sensor can be configured to output an impedance signal via the plurality of electrodes to the body of the patient. The plurality of electrodes can be configured to receive from the body of the patient an electrical signal comprising an electrocardiogram (ECG) signal and a modulation of the impedance signal. The patient status sensor also comprises a processor disposed in or on the substrate, and the processor can be configured to: receive and process the electrical signal to determine a measurement of heart rate from the ECG signal and respiration rate from the modulation of the impedance signal; determine patient status based at least in part on (a) the measurement of the heart rate and one or more heart rate limits and (b) the measurement of the respiration rate and one or more respiration rate limits; and output a patient status signal to the visual indicator in response to the determination of the patient status. The visual indicator can be configured to output visual information indicative of at least one of the heart rate, the respiration rate, and the patient status. The patient status sensor can also comprise a power source disposed in or on the substrate. The power source can be configured to be electrically connected to the plurality of electrodes, the visual indicator, and the processor.

DETAILED DESCRIPTION OF PREFERRED EMBODIMENTS

Figure 1:
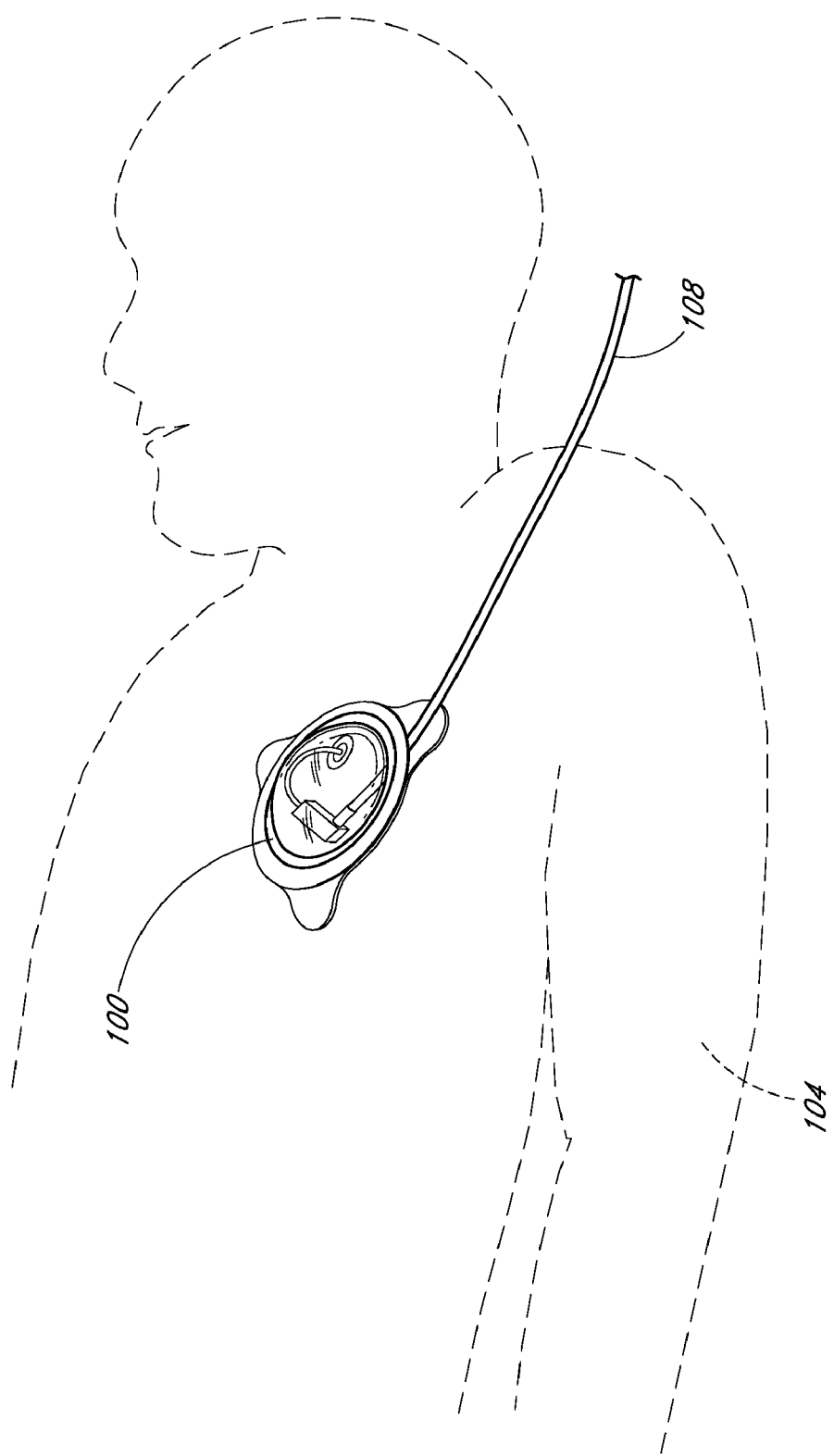
FIG. 1 shows an example of an intraosseous (IO) fluid delivery system applied to the sternum of a patient and an infusion tube connected to a sternal access portal introduced into the sternum of the patient. An infusion fluid can be delivered via the tube through a lumen in the sternal access portal and into bone marrow.

The following detailed description is directed to certain specific embodiments. However, the teachings herein can be applied in a multitude of different ways. In this description, reference is made to the drawings wherein like parts are designated with like numerals throughout.

Overview of Embodiments of Patient Vital Signs Monitoring Systems

Many traditional monitoring methods and systems for vital signs in the field are complicated and may involve the use of portable devices weighing several pounds along with multiple sensors and cables. In battlefield situations and traumatic events, many seriously injured patients may be in the same area. Several monitors would be desired when only one is present. In addition, several vital signs with individual cables and connections must be continuously monitored to determine the status of each patient.

Examples of vital signs that can be measured to monitor patient status include: electrocardiogram (ECG or EKG), saturation of peripheral oxygen (SpO2), blood pressure, respiration, temperature, heart rate, blood glucose, pH, etc. Certain traditional methods and devices for measuring vital signs suffer from disadvantages.

ECG can be used to determine the pulse rate and rhythm as well as rhythm abnormalities. ECG measurements may use electrodes to pick up the electrical impulses on the skin and cables to connect between the electrodes and the patient. Many wireless methods can be used to eliminate or reduce reliance on cables (for example radio-frequency (RF) technologies such as, e.g., Bluetooth or 802.15.4 ZigBee). In some cases, wireless methods can have power and interference issues and tend to be rather more expensive than the cables they replace. An example is Alive Technologies' Heart Monitor (Arundel Queensland, Australia).

Temperature sensors may also use cabling. In some implementations, temperature sensors do not use the same electrode sites as ECG since body surface temperature measurements may have a poor relationship to the body's internal temperature, especially on patients in shock. In some cases, a temperature sensor is placed in an alternative anatomical location and uses a separate cable or an additional wireless component.

Blood pressure is traditionally measured using an inflatable cuff using either hand-operated or electronic pumps. Blood pressure devices may be configured to deliver systolic, diastolic and mean pressures along with pulse rate while the measurement is being taken. In some implementations, the pulse rates measured are periodic, not continuous, since pulse rates are measured only when the cuff is deflating. Many such units tend to be bulky, use even more power than other sensors, and use a cuff or mechanism encircling an arm or a leg. Access to the appropriate arm or leg site may not be possible in trauma situations due to injuries, especially if tourniquet(s) have been applied to the patient.

SpO2 can be measured using pulse oximetry sensors and electronics to determine blood oxygen levels and can also return a pulse rate and patient peripheral circulation. Nonin Medical, Plymouth, Minn., provides wireless pulse oximetry products that use Bluetooth wireless technology.

Respiration can be monitored using several methods including, for example, body impedance. In some implementations, body impedance can be obtained using the ECG electrodes. Respiration may also be monitored using other technology utilizing a separate connection or cable.

These traditional methods generally use a patient monitoring device to collect and display the vital signs obtained from sensors. The monitoring device can be a battery powered device with a display large enough for good viewing at an appropriate distance. The physician or paramedic views the display and interprets multiple waveforms and measurements or listens to the audible sounds (e.g., beeping) to determine the status of the patient.

An example of a patient monitoring system is the Propaq® LT monitor available from Welch Allyn Protocol Systems (Skaneateles Falls, N.Y.). The Propaq monitor can be used in military and EMS applications to monitor trauma patients and has multiple channels of ECG along with temperature, blood pressure, and pulse oximetry.

While certain vital signs monitoring systems are certainly useful in some situations, the systems are typically large, use multiple connections, have large displays, lots of cabling, and deliver a complex display that may be difficult to interpret quickly to assess the basic status of a trauma patient. Monitoring systems using wireless communication technology exist but wireless communication may add expense and complexity. It may be too expensive for emergency medical personnel to have enough of these monitors for large-scale traumatic accidents. These monitors may take significant time to connect to a patient and properly configure. Even when properly set up, many of these monitors require significant training to use and constant observation to obtain the status of a given patient. Various embodiments of the systems and devices described herein may address some or all of the above challenges and/or other challenges.

Overview of Intraosseous Systems and Methods

Intraosseous (IO) fluid delivery systems are used for the delivery, injection, or infusion of medications, fluids, or blood products, typically directly into the marrow of a bone. IO methods typically penetrate long bone or sternal bone by introduction of a hollow bone portal into the marrow space. IO infusion or delivery systems can provide rapid vascular access for fluid and drug infusion in patients, for example, shock and trauma victims and can be an alternative to conventional intravenous and central lines. IO systems may also provide associated connections and tubing and mechanical fixation for the tubing. For example, a portion of the IO delivery system may be secured to the patient's skin with an adhesive system. IO systems can be used in trauma or battlefield conditions where traditional patient monitoring devices can be used to monitor vital signs such as, e.g., pulse, ECG, blood pressure, temperature, and other patient parameters are not accessible or are difficult to use. IO systems may be used to deploy high drug concentrations quickly into the central circulation.

Certain IO access and delivery products are available. For example, the EZ-IO® System is available from Vidacare Corporation (San Antonio, Tex.), and the FAST1® or FASTx™ Intraosseous Infusion System is available from Pyng Medical Corporation (Richmond BC, Canada). Sternal IO may be an advantageous method of access in traumatic injury due to inaccessible or non-patent peripheral access. Limbs may be injured or amputated, and traumatic conditions like shock can make it difficult to start IV access. In some implementations, sternal access can involve inserting a bone portal through the bone to provide access to the marrow. For example, fluid can be delivered through an infusion tube attached to a proximal end of the bone portal. The fluid can flow through a delivery channel in the bone portal (e.g., a lumen or bore) and into the highly perfused marrow and subsequently into the blood stream. For example, the Pyng FAST1® or FASTx systems use a mechanical introducer to place a bone portal into the sternal bone marrow space. The bone portal delivery system can be used with an adhesive patch to configured to assist a medical attendant in positioning the bone portal in a desired location on the bone (e.g., between the xyphoid process and the sternal notch). The Vidacare EZ-IO® system generally provides access into the marrow space of long bones (e.g., tibia, humerus) using a drill-like device to introduce a hollow needle or portal through the bone. A catheter can be attached to the proximal end of the needle or portal to introduce fluids into the IO space.

FIG. 1 shows an example of a sternal IO delivery system 100 comprising an adhesive patch applied to the sternum of a patient 104. The IO delivery system 100 includes a bone portal inserted into the sternum (the bone portal is not visible in FIG. 1). FIG. 1 also shows an infusion tube 108 connected to the IO delivery system 100. The adhesive patch comprises an access opening through which the bone portal can be placed in the bone using a mechanical introducer (not shown in FIG. 1). The patch of the IO delivery system 100 comprises an adhesive component that adheres the patch to the patient's chest.

Patients receiving IO lines often have traumatic injuries and are in shock or very unstable. These lines are often inserted under dangerous or complex situations. Medical staff who deliver treatment to multiple patients simultaneously need the ability to quickly assess the status of the each patient to decide which patient to treat and which patients are stable enough. A quick and simple assessment and continuous monitoring of the status of these patients can be useful for good treatment of the patient.

Example IO Patient Status Sensor Embodiments

In view of the aforementioned, embodiments of a patient status sensor are provided that can be applied to a patient or trauma victim to provide a quick visual indication of the patient's vital signs (e.g., respiration, heart rate, or other vital signs). Certain embodiments can be configured as an adhesive patch that includes electrodes for measuring heart rate (and respiration in some implementations), a processor configured to perform calculations for determining one or more vital signs using information from the electrodes, and audible or visual indicators to communicate information about vital signs or patient status to a medical attendant. Certain embodiments can include an access opening to allow for intraosseous delivery of fluids to bone marrow (e.g., through sternal or long bone). Certain such embodiments may be used with an IO delivery system configured to provide fluid to bone marrow. Certain embodiments include wired or wireless components to communicate vital signs or patient status to an external monitoring device. Many variations of the patient status sensor are contemplated, and various embodiments will be further described below.

Figure 2:
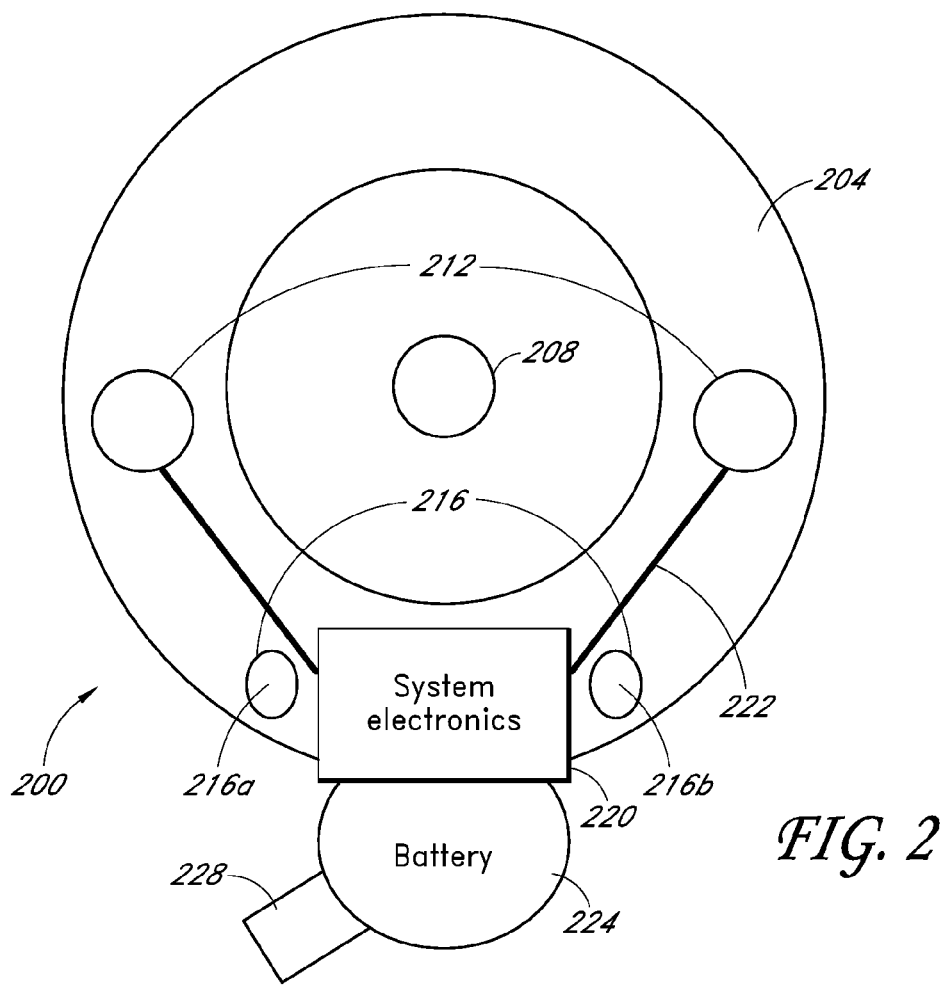
FIG. 2 is a top view that schematically illustrates an embodiment of a patient status sensor comprising a patch that can be used with various embodiments of an IO delivery system.

FIG. 2 is a top view that schematically illustrates an embodiment of a patient status sensor that comprises an IO patch 200. The IO patch 200 can be configured to be applied over the manubrium of a patient to provide a location for access to sternal bone marrow. For example, the IO patch 200 can be placed between the xyphoid process and the sternal notch on a patient's chest. In other embodiments, the IO patch 200 can be configured to be applied over a different bone of the patient (e.g., a long bone). The IO patch 200 comprises a flexible substrate 204 that can conform to the contours of a patient's skin. The substrate can be shaped substantially circularly (e.g., as shown in FIG. 2) or can be shaped to include markers or other indicia to assist positioning the patch 200 properly on the patient (e.g., for anatomical location assistance and/or patch alignment). The patch 200 may have a diameter in a range from about 1 inch to about 6 inches in various embodiments.

The patch 200 may comprise an adhesive component to adhere the patch to the patient's skin. For example, the lower surface of the patch 200 comprises an adhesive layer or adhesive gel (e.g., the substrate may comprise a foam-backed adhesive) to adhere the patch 200 to the skin of a patient. The lower surface can be covered by a removable (e.g., peel-off) layer to protect the adhesive when the patch 200 is not in use. The substrate 204 may comprise other materials including, e.g., cloth or plastic backing materials with an adhesive for application to the patient's body. For example, in some embodiments, the patch is configured similar to 3M Red Dot electrodes available from 3M Corporation (St. Paul, Minn.). In various embodiments, the patch 200 can be configured as a disposable for a single-use. The patch 200 can be provided in a sterile package. In some embodiments, the patch 200 and some or all of the components of an IO delivery system can be provided in the sterile package. For example, the package may include the patch 200, a mechanical introducer for introducing the bone portal into the bone, and a conduit (e.g., tubing) for delivery of infusion fluids.

Figure 2A:
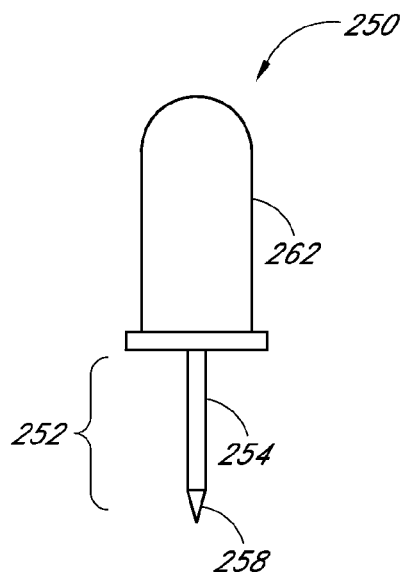
FIG. 2A schematically illustrates an embodiment of an IO delivery system comprising an embodiment of a patient status sensor.
Figure 2A:
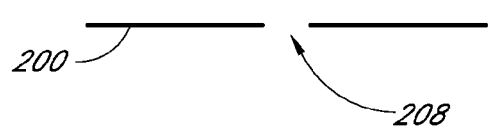

In the illustrated embodiment, the patch 200 comprises an IO access opening 208 that can be used with IO delivery components. For example, an IO needle or bone portal can be inserted through the opening 208 and introduced into the patient's bone. As schematically illustrated in FIGS. 2 and 2A, an IO delivery system may comprise the patch 200 and an introducer 250 configured to introduce a bone portal 258 into a bone. The introducer 250 can comprise a sleeve 262 and a needle assembly 252. The needle assembly 252 can comprise an infusion conduit 254 coupled to a proximal end of the bone portal 258. The infusion conduit 254 may comprise flexible tubing. A medical attendant can position the introducer 250 over the opening 208 of the patch 200 so that the bone portal 258 passes through the opening 208. Force applied to the sleeve 262 urges the bone portal 258 through the patient's skin and into the bone. For example, in some embodiments, the needle assembly 252 comprises a needle or stylet (not shown in FIG. 2A) that passes through the infusion conduit 254 and contacts the proximal end of the bone portal 258. The needle or stylet transfers a user-applied force to the proximal end of the bone portal 258 to cause the distal end of the bone portal 258 to penetrate the bone (e.g., the sternum or a long bone).

The distal end of the bone portal 258 may have a sharp point or be conically tapered to assist insertion of the bone portal 258 through the patient's skin and into the bone. After insertion of the bone portal 258 into the bone, the needle or stylet can be removed from the infusion conduit 254, leaving the bone portal 258 in the bone. The bone portal 258 can comprise a fluid delivery channel (e.g., a lumen or bore) such that fluids can be introduced to the bone marrow via the infusion conduit 254, which can be coupled to the proximal end of the portal 258. The IO delivery system may include a remover that can be used to remove the bone portal 258 from the bone. For example, the remover may comprise a threaded rod configured to engage complementary threads in the proximal end of the fluid delivery channel of the bone portal 258. The remover can be used to pull the bone portal 258 out of the bone. In other embodiments, a remover is not used to remove the bone portal 258, which may be removed, for example, by pulling firmly on the infusion conduit 254.

Examples of IO delivery components, introducers, bone portals, infusion tubing, removers, and so forth that can be used with embodiments of the patient status sensors disclosed herein are described in, e.g., U.S. Pat. No. 5,817,052, entitled "Apparatus for Intrasosseous Infusion or Aspiration," U.S. Pat. No. 6,761,726, entitled "Method and Apparatus for the Intraosseous Introduction of a Device Such as an Infusion Tube," U.S. Pat. No. 7,347,840, entitled "Patch for Locating a Target Zone for Penetration," and U.S. Patent Publication No. 2008/0208136, entitled "Bone-Penetrating Member for Intraosseous Infusion and Aspiration Devices," each of which is expressly incorporated by reference herein in its entirety for the material specifically referred to herein and for all other material that it discloses. In other implementations, portions of the introducer may not be a separate component but may be integrated with the patch 200. In various implementations, embodiments of the patient status sensor 200 can be used with the FAST1® or FASTx™ Intraosseous Infusion System available from Pyng Medical Corporation (Richmond BC, Canada) or with the EZ-IO® System available from Vidacare Corporation (San Antonio, Tex.).

In other embodiments, the patch 200 does not include the IO opening 208 and provides patient sensing capabilities without IO access. For example, in large scale trauma situations certain such embodiments could be deployed independently of an IO system in order to provide vital signs monitoring.

In various embodiments, the patch 200 comprises electronics 220 and a power source 224 (e.g., a battery, fuel cell, etc.). The patch 200 may be used with components used for the IO delivery system and/or sensors integrated with the IO bone portal that is to be delivered with the sternal or long bone IO system. The patch 200 comprises electrodes 212 to establish an electrical connection with the skin for measuring ECG (and respiration in some implementations). For example, the electrodes 212 can comprise silver/silver chloride (Ag/AgCl) ECG electrodes. In some embodiments, the electrodes 212 are integrated into the substrate 204 or an adhesive component of the patch 200, e.g., an adhesive material on the lower (skin-side) surface of the substrate. In some implementations, a feed-through, riveted button, or flexible circuits 222 provide electrical communication to the electronics 220 so that body-surface ECG signals can be transmitted from the electrodes 212 to the electronics 220. Although the embodiment of the patch shown in FIG. 2 comprises two electrodes 212, in other embodiments, a different number of electrodes can be used (e.g., 1, 3, 4, 5, or more). Also, the location of the electrodes 212 on the patch 200 can be different than shown in FIG. 2. In some implementations, electrical connections with the patient's skin can be made (additionally or alternatively) using belts or straps to position electrical contacts, plates, or electrodes on the skin. In some embodiments, the electrodes 212 are formed from flexible materials.

The embodiment of the patch 200 shown in FIG. 2 also comprises a patient status indicator 216. The status indicator 200 can include one or more audible indicators, one or more visual indicators, or a combination of audible or visual indicators to indicate information relating to patient status (e.g., one or more vital signs). In the illustrated embodiment, the status indicator 216 comprises two light emitting diodes (LEDs) 216a and 216b. The visual status indicators can be configured to display one or more colors. For example, in the illustrated embodiment, the LED 216a emits green light and the LED 216b emits red light, although additional or different colors can be used in other embodiments. In some embodiments, one or more of the LEDs 216a, 216b can comprise a high-brightness LED to improve visibility in bright conditions. Other types of electroluminescent sources can be used. Visual status indicators can include a display (e.g., a liquid crystal display (LCD)) to indicate patient status information (e.g., alphanumeric information, graphical icons, trend lines, etc.). In some embodiments, one or more visual status indicators may blink, flash, or be time variable to indicate patient status or changes in patient status (e.g., blink at the patient's heart rate or respiration rate). In some implementations, one or more visual status indicators may be activated only at certain times (e.g., if a patient's condition changes to critical, a red indicator may be displayed).

One example implementation utilizes a patient status indicator comprising three LED indicators, for example, a green LED to indicate patient status is stable, a yellow LED to indicate patient status is unstable, and a red LED to indicate patient status is deteriorating or emergency status. One or more of these LEDs may blink or provide a time-variable brightness. Illumination or a change in brightness may be used to indicate quality of signal for a vital sign or that vital sign information has been measured. In some implementations, the yellow LED is not used (see, e.g., the embodiments shown in FIG. 2). Many variations and combinations of light sources are possible. Since the patient status sensor can be used in battlefield situations, the patient status sensor can comprise one or more LEDs that emit light in the infrared (IR) spectrum. Such implementations may allow the patient status sensor to be more discrete (and not visible to eyes of opposing combatants), but visible to electronic visual augmentation devices worn by medical attendants. The patient status sensor optionally may utilize a switch to disable or reduce the output of the visual indication (and/or audible indication) entirely if desired. In some embodiments, one or more multicolor LEDs or white light LEDs can be used to provide visual indication of patient status. For example, an array of light sources may be used, and one or more of the light sources illuminated to indicate a desired pattern.

The patient status indicator 216 may include one or more audible indicators that sound a beep, a tone, or signal. For example, an audible indicator may provide sounds to indicate a vital sign (e.g., beep at the patient's heart rate or respiration rate) or may provide a sound or warning signal if the patient's condition changes (e.g., deteriorates or improves). In some embodiments, tone and/or duration of the audio signals provided by the audible indicator are related to patient vital signs (e.g., heart rate, patient condition, etc.) and are used to alert a physician or medic to patients needing immediate attention. In some embodiments, the electronics 220 includes a speech or voice synthesis component so that an audible indicator can provide a voice status message. A switch may optionally be added to the patch 200 to silence or mute audio output when desired such as, e.g., for battlefield usage.

In some embodiments, the audible indicator comprises a piezo-electric component, which advantageously is relatively low-cost. The audible indicator may comprise a speaker. In various embodiments, one or more of the patient status indicators 216 can be integrated into the substrate 204 or the adhesive of the patch 200.

The patch 200 comprises the power source 224, which may comprise a battery. For example, the battery can be a commercial long-lifetime battery with a low self-discharge rate. Examples include coin cell lithium batteries used in hearing aides and watches (e.g., CR032 or CR2032). The patch 200 may include an activation pull tab 228 which keeps the power source 224 electrically disconnected during manufacture, shipping, and storage. The pull tab 228 can include an electrically insulating material such as, e.g., Mylar, that prevents conductive contact from occurring and reduces the likelihood of battery discharge during storage. The tab 228 can be pulled from the patch 200 and discarded, allowing the battery to be electrically connected to the electronics 220 so as to activate the electronics on the patch 200. In some embodiments, the pull tab 228 is integrated with the packaging for the patient status sensor 200 so that the pull tab 228 is automatically pulled without further user intervention when the packaging is opened.

In the embodiment illustrated in FIG. 2, the patch 200 includes integrated electronics 220 used to monitor patient status, but does not include sensors for providing feedback on delivery of fluids via the IO opening 208. Feedback on delivery of fluids may be provided in other embodiments, for example, to provide feed back to indicate a clogged tube or access.

Certain embodiments of an IO delivery system can include an adhesive component configured to adhere a portion of the IO delivery system to the skin of the patient. In certain such embodiments, the electrodes 212, the system electronics 220, and the power source 224 can be disposed in or on the adhesive component to provide vital sign monitoring and patient status sensing capabilities to the IO delivery system. In other embodiments, the components may be configured differently. For example, the electrodes 212 may be disposed in or on the adhesive component, and the system electronics 220 and/or the power source 224 may be disposed elsewhere in the IO delivery system (e.g., on an introducer or sleeve used to position the IO delivery system or to provide force to introduce a bone portal to the bone). Many variations are contemplated, and embodiments of the disclosed patient status sensor can be configured for use with a wide variety of IO delivery systems.

Figure 3:
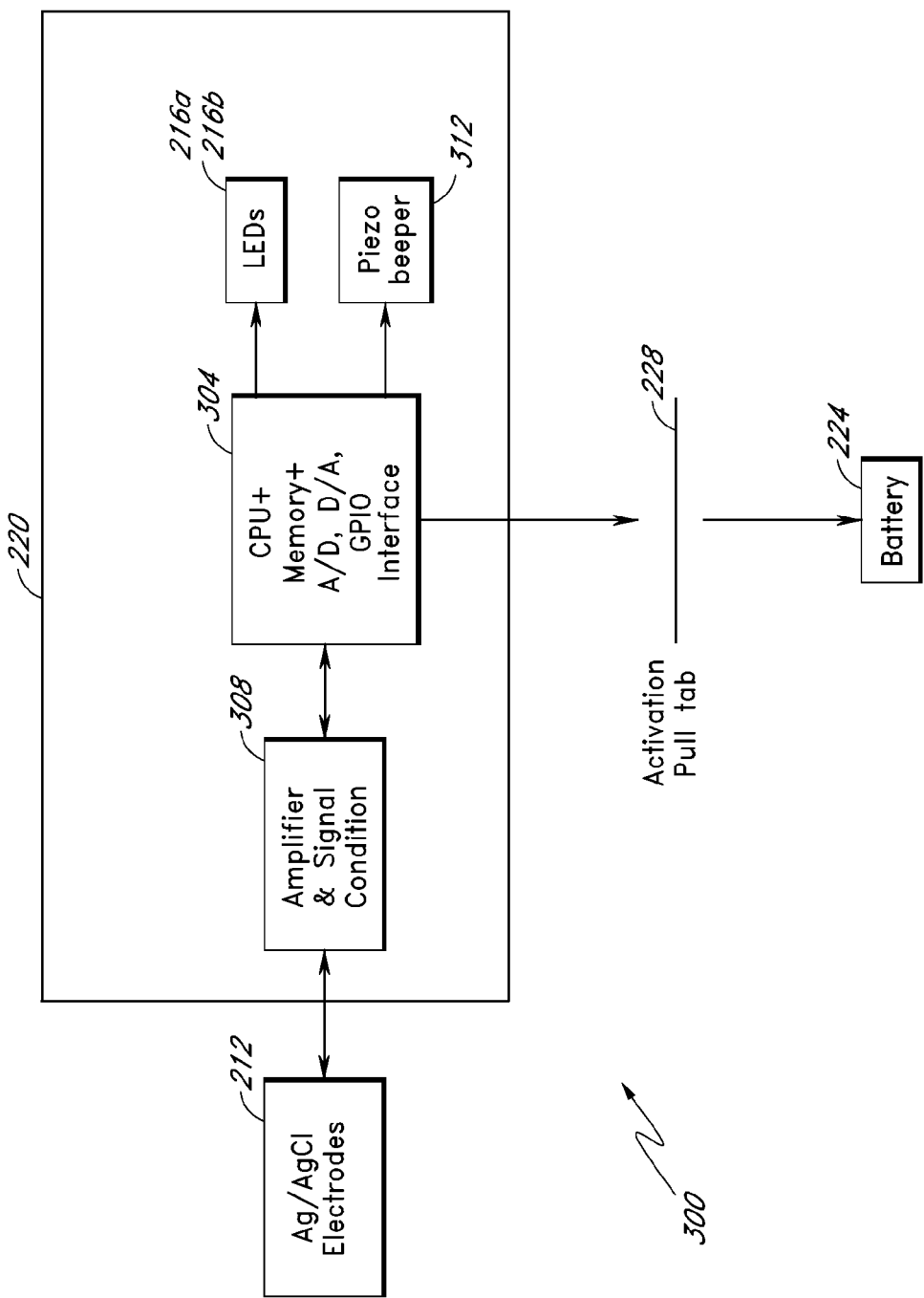
FIG. 3 is a block diagram that schematically illustrates an embodiment of circuitry for a patient status sensor. The circuitry can process body signals to determine heart rate (among other vital signs) and to determine patient status based at least in part on the heart rate (or other vital signs).

FIG. 3 is a block diagram that schematically illustrates an embodiment of a patient status sensor 300 that includes the system electronics 220. In this embodiment, the system electronics 220 comprises a processor 304, an amplifier and signal conditioner 308, the visual indicators (e.g., LEDs) 216a, 216b, and an audible indicator (e.g., a piezoelectric beeper) 312. One example implementation uses simple low-power, low-cost components to implement the system electronics 220, since high fidelity signals are not needed for certain patient monitoring applications. In the illustrated embodiment, the amplifier and signal conditioner 308 amplifies and conditions the signals from the electrodes 212. In other embodiments, the amplifier and signal conditioner 308 may be integrated with the processor 304 or not used at all. Signal processing is performed in the processor 304, which may include a CPU, storage/memory (e.g., RAM, ROM, EEPROM, flash), general purpose input/output (GPIO), analog-to-digital (A/D) and digital-to-analog (D/A) converters, digital signal processors (DSP), and so forth. In some embodiments, the processor 304 comprises a high-integration, low cost microprocessor such as, e.g., the Texas Instruments (TI) MSP430 family of processors (e.g., an MSP430FG439). One example of a microprocessor implementation that can be used in certain embodiments of the electronics 220 is described in the TI report: "Application Report SLAA280A—October 2005, Revised September 2007, Heart-Rate and EKG Monitor Using the MSP430FG439" by Murugavel Raju, which is hereby incorporated by reference herein in its entirety. In some embodiments, the electronics 220 may comprise a digital signal processor (DSP), a field-programmable gate array (FPGA), an application-specific integrated circuit (ASIC), and/or a programmable logic device (PLD) in addition to or instead of a microprocessor.

In some implementations, the processor 304 includes an integrated analog-to-digital converter (A/D), and signals from the amplifier and signal conditioner 308 may be digitized by the A/D. The processor 304 may be configured to execute software code modules or instructions that process the signals to determine one or more vital signs (e.g., to calculate heart rate, respiration rate, patient status or condition, etc.). In some embodiments, the software code modules may extract signal components to identify certain rhythms and morphologies indicative of degraded or emergency patient status.

The processor 304 can be programmed to determine the status of a patient based at least in part on the signals from the electrodes 212. For example, patient status can be based at least in part on one or more vital signs, changes in vital signs, trends in vital signs, or combinations thereof. Patient status may include, for example, whether the patient is stable or unstable. In some implementations, setpoints for low and/or high heart rate (or other vital signs) can be used to indicate patient status. In some implementations, rhythm and morphology analysis techniques similar to those used in, for example, Holter and event monitors are used to determine patient status. Other vital signs may also yield measurements that have normal or abnormal readings for comparison and status determination.

In some embodiments, combinations of the vital sign measurements and trends can be used for stability analysis algorithms and determinations. In some such embodiments, this data can be algorithmically combined to give a patient status indication, e.g., green (good), yellow (concern), or red (emergency) status. In some implementations, the processor 304 communicates the determined patient status to medical professionals using status indicator 216.

Embodiments of Vital Sign Transmission and Display

In some embodiments, patient status, vital signs, and/or other information may be communicated from the patient status sensor to external devices using wired and/or wireless transmission methods. For example, one possible implementation can include the addition of a transmission system comprising further device components that can transmit the patient information using technology for frequency modulation (FM) or amplitude modulation (AM) of an audio signal based on the magnitude of a vital sign (e.g., ECG) over time. A speaker or audio output device on the patient status sensor can be used to output the audio signal. Examples of such a technique are used in transtelephonic ECG transmission products such as, e.g., Aerotel Medical Systems' Heartline products (Holon, Israel) or the IM1200 Transtelephonic Receiver from Integrated Medical Devices, Inc. (Liverpool, N.Y.). Other audio transmission techniques can be used.

In some embodiments, the audio signal may comprises frequencies that are outside of normal hearing range (e.g., ultrasonic or megasonic frequencies). The audio signal may be used to communicate analog and/or digital information encoded using frequency or amplitude encoding methods.

Figure 4:
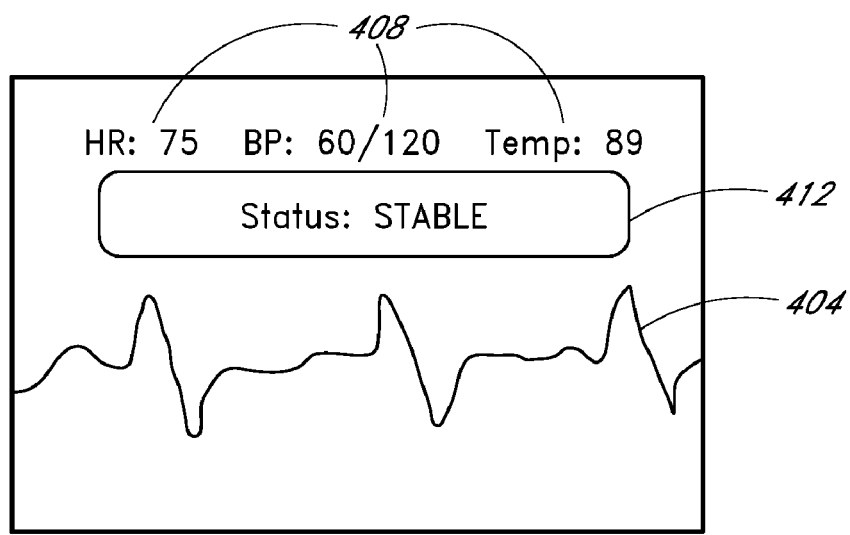
FIG. 4 is an example of a graphical user interface that can be displayed on a monitoring device to indicate vital signs and patient status.

In some implementations, a microphone integrated in a monitoring device, a personal digital assistant (PDA), a cellular telephone, a smart phone (or any other hand-held or portable computing device) receives the audio signal from the patient status sensor. Software on the monitoring device decodes the audio signal and processes and/or displays the information related to patient status. In other embodiments, the audio signal can be transmitted by cellular or radio connection for decoding/processing remotely, and the decoded information returned to the device for display. Methods used to decode the signal can include both software implementations and hardware implementations. FIG. 4 is an example of a graphical user interface 400 that can be displayed on the monitoring device (or on the patient status monitor) to indicate vital signs and patient status. In this example, the user interface 400 includes an ECG trace 404, information on vital signs 408, and an indication of patient status 412 (e.g., Stable). In this example, the vital sign information 408 shows heart rate (e.g., HR: 75) in beats per minute, blood pressure (e.g., BP: 60/120) showing systolic (e.g., 120) and diastolic (e.g., 60) pressures in mm Hg, and body temperature (e.g., 89) in degrees Fahrenheit.

In some embodiments, wireless technologies could be employed, additionally or alternatively, to the audio transmission methods described above. For example, wireless transmission may be advantageous to provide silent transmission or for transmission over longer distances. Wireless methods can include RF wireless technologies such as ZigBee (IEEE 802.15.4), WiFi (IEEE 802.11), WiMax (IEEE 802.16), Bluetooth (IEEE 802.15.1), cellular, or custom implementations. In some such RF wireless implementations, the patient status sensor comprises wireless transmission circuitry and an antenna to transmit vital signs or patient status information to one or more suitable receivers, which may process and/or display the information. In some embodiments, visible or infrared LEDs used for status indication could be used for transmission using Infrared protocols designed for Infrared Data Association (IrDA) transmission.

Embodiments providing utilization of RF wireless technologies may enable a larger system network or aggregation comprising one or more patient status sensors linked to an aggregator device that could combine the data from the sensors. The aggregator device may provide a remote linkage utilizing cellular or wide area networking technologies. In some such embodiments, location localization techniques could identify status and/or position of the patient status sensors and help coordinate relief efforts on a larger geographical scale. The aggregator device may comprise one or more general and/or special purpose computers or processors that may perform some or all of the processing functions described herein.

Additional Patient Status Sensor Examples and Embodiments

In various embodiments, the patient status sensor may include additional or different functionality than described above. For example, measurement of respiration may be provided through the ECG electrodes 212 by measuring variations in body impedance that occur when the lungs expand (e.g., impedance pneumography). D/A channels on the processor 304 may be utilized to produce an alternating current (AC) signal that is communicated to and transmitted through the ECG electrodes to the patient. Resulting signals from the patient can be measured when acquired with the ECG signal. In some cases, the body impedance signal can be separated from the ECG signal using signal processing methods such as, e.g., filtering.

Figure 5:
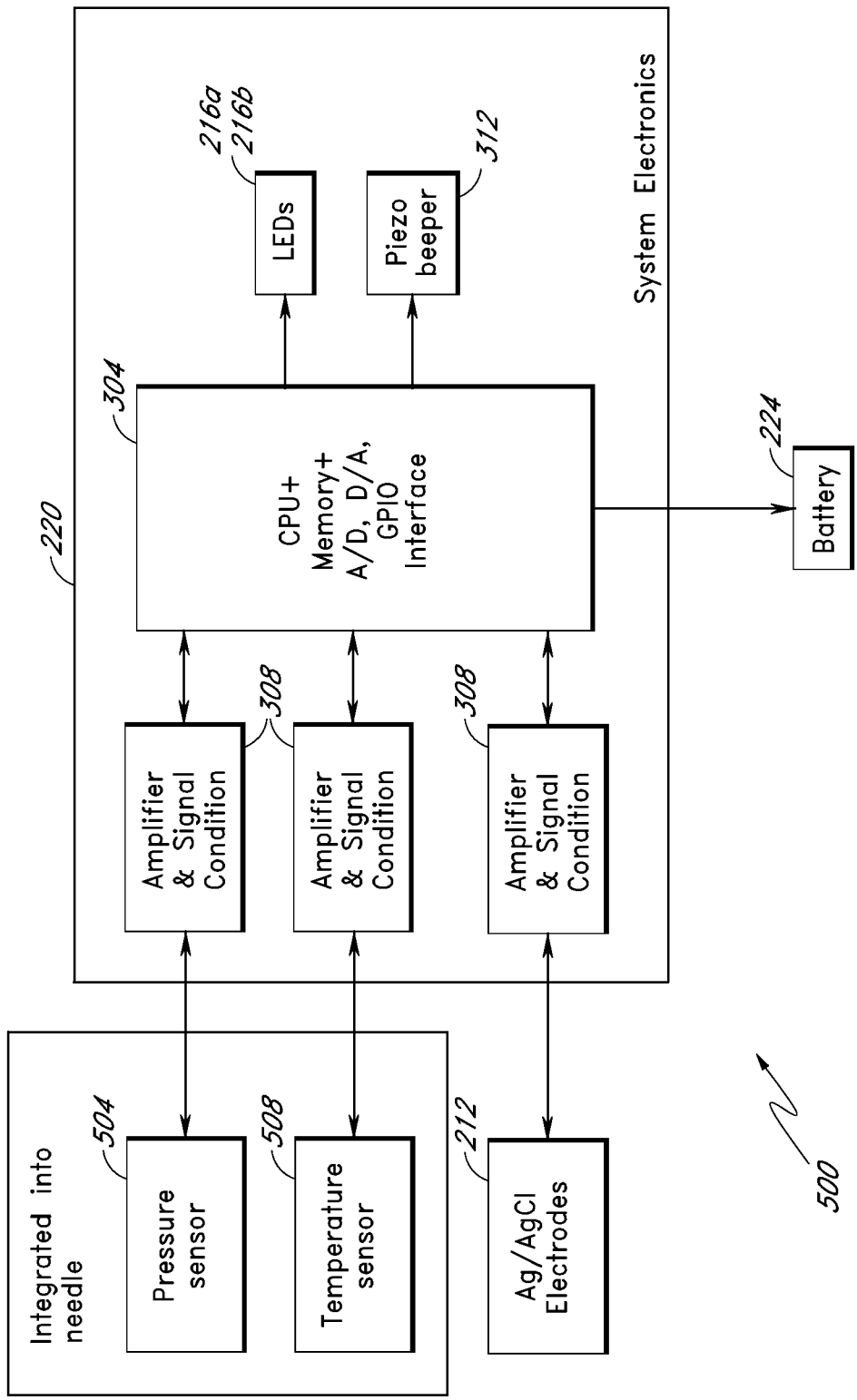
FIG. 5 is a block diagram that schematically illustrates an embodiment of circuitry for a patient status sensor comprising a pressure sensor and a temperature sensor that can be integrated or used with IO delivery components.

In some example implementations, one or more analyte sensors may be introduced with the IO needle assembly, either as an additional needle or integrated into the primary IO needle or a bone portal. These analyte sensors include those utilized for additional vital signs. For example, FIG. 5 is a block diagram that schematically illustrates an embodiment of a patient status sensor 500 comprising a pressure sensor 504 that can be integrated with an IO needle assembly or bone portal to provide the IO pressure. For example, as described herein, the bone portal may comprise a fluid delivery channel (e.g., a lumen or a bore) to deliver fluid to the bone marrow. In some embodiments, the pressure sensor (or other analyte sensor) is disposed on an inner surface of the delivery channel adjacent the distal end of the bone portal. Such embodiments advantageously may reduce the likelihood of damage to the sensor when the bone portal is inserted into the patient's bone. In other embodiments, the pressure sensor (or other analyte sensors) can be disposed in a different location on the bone portal (e.g., other portion of the needle assembly). Accordingly, in some such embodiments, the pressure sensor has access to fluid in the marrow and can make a measurement of the pressure of the fluid. This pressure is correlated with and can be used to infer blood pressure. The IO delivery system may include circuitry (e.g., wires) to electrically connect the pressure sensor (or other analyte sensor) to the system electronics 220 so that the processor 304 can process the pressure signal (or other analyte sensor signal) to determine blood pressure (or other vital sign). In some embodiments, multiple analyte sensors are disposed in or on the bone portal or needle assembly of an IO delivery system.

Measurement of the pressure may provide an alternative to ECG for measuring pulse rate. In some embodiments, the pressure sensor 504 can be used to monitor the patient blood pressure and is not be used to provide feedback on delivery of fluids. In other embodiments, the pressure sensor can be used to provide feedback on fluid delivered to the patient via the IO needle. The processor 304 can be programmed to measure the pressure signal and determine patient blood pressure.

Other sensors can be used. For example, a pressure sensor or flow sensor may be used to provide status as to the patency of the IV and portal in use. Such measurements may be used to alert the physician or medic that there may be an issue requiring immediate attention (e.g., via activating one or more patient status indicators). A temperature sensor 508 can be integrated with the IO needle assembly or bone portal to provide measurements of core body temperature. For example, as discussed above for the pressure sensor, a temperature sensor (e.g., a thermistor) can be disposed on a distal end of the bone portal (e.g., disposed on an inner surface of the delivery channel of the bone portal). A temperature sensor can be integrated into the patch 200 (e.g., in the substrate 204 or adhesive) to provide measurements of skin temperature. Many variations are possible.

For example, some embodiments are configured to perform pulse oximetry to measure SpO2. Such an embodiment can include one or more photoemitters and one or more photodetectors to measure absorption by pulsing arterial blood of light (e.g., red and infrared light) emitted by the photoemitters. The absorption measurements can be used to infer oxygenation of the blood (e.g., SpO2). In other embodiments, blood oxygen can be measured using a blood oxygen sensor integrated with the IO needle assembly or bone portal (e.g., a blood oxygen sensor disposed adjacent a distal end of the bone portal).

The patient status sensor can be used in a variety of implementations. One example implementation provides for low cost, very low power devices and focuses on the IO sternal systems, IO long-bone systems, or other IO systems. Although various example implementations have been described in the context of IO systems, other implementations such as stand-alone systems would have benefits. Embodiments of the devices and systems disclosed herein are not required to be used with IO systems and can be used with any other medical device or procedure (see, e.g., discussion of embodiments with reference to FIG. 6). Embodiments of the patient status sensor can be of great utility in medical care situations such as hospital emergency rooms, nursing homes, and remote care clinics. Embodiments of the patient status sensor could be used by emergency medical personnel (e.g., paramedics, first responders, police, or fire fighters) at trauma sites (e.g., automobile crashes, fires, etc.). The ability of certain sensor embodiments to send data to a wirelessly connected device such as a smart phone, medical device monitor, computer processor, etc. allows remote diagnosis and assistance from more highly trained medical personnel. Other implementations are possible.

Embodiments of Standalone Implementations of a Patient Status Sensor

Certain embodiments of the patient status sensor are not configured for use with an IO fluid delivery system. Accordingly, certain such embodiments do not include the IO opening 208 shown in FIG. 2. Certain such embodiments also may not include wired or wireless communication components on the sensor. Certain such embodiments may be referred to as standalone sensors. Various embodiments of standalone sensors may offer some or all of the following advantages depending on how the sensor is configured: low-cost, lightweight, easy to use, long storage lifetime, no wires to tangle, no "off-sensor" wireless handshaking or communications protocols to establish, no interference with medical treatments or complications for patient transport, etc. Standalone sensors having a wide range of configurations are contemplated.

Figure 6:
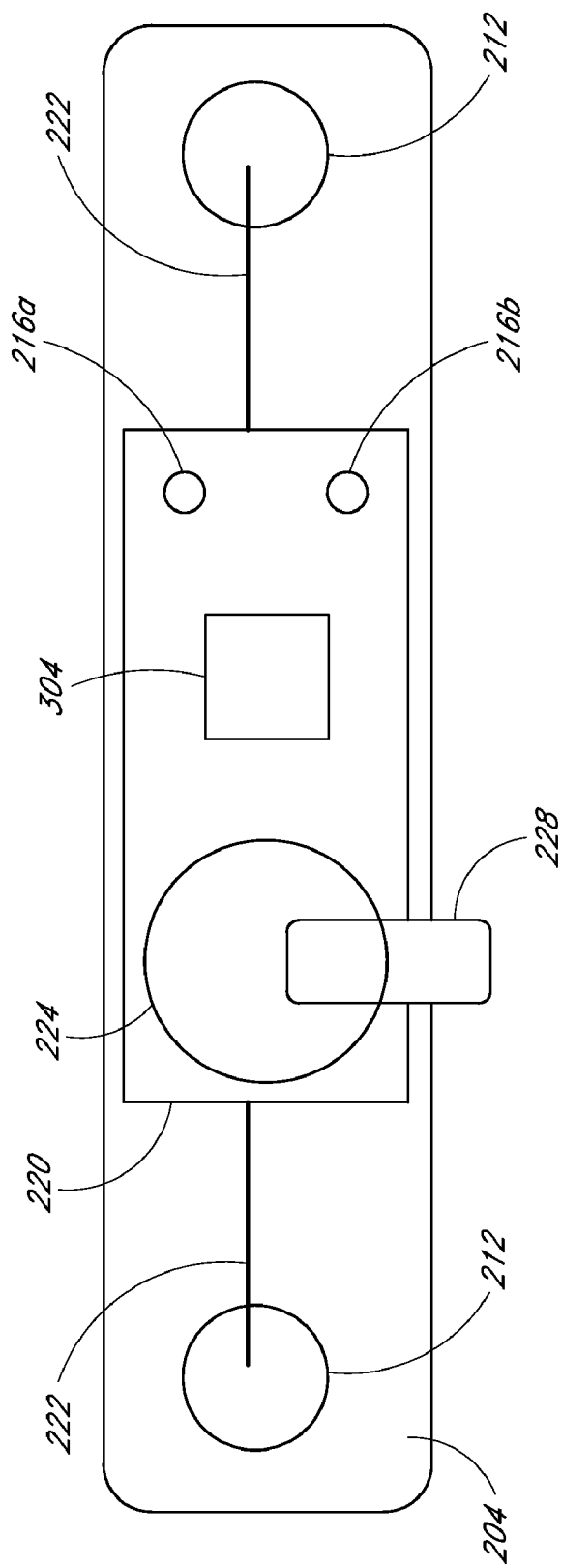
FIG. 6 is a top view that schematically illustrates an embodiment of a standalone patient status sensor.

FIG. 6 schematically illustrates an embodiment of a standalone patient status sensor 600. In this example embodiment, the sensor 600 includes electrodes 212, power source 224, processor 304, LEDs 216a, 216b, and flexible circuitry 222 in or on the substrate 204. The components schematically illustrated in FIG. 6 may be generally similar to the components described with reference to FIG. 2. In the illustrated embodiment, the substrate 204 comprises a foam-backed adhesive component that can conform to the patient's body. The electrodes 212 are embedded in the adhesive component. The substrate 204 can be shaped substantially as a rectangle. For example, the substrate 204 may be sized and shaped similarly to a band-aid, and the adhesive surface of the substrate may be covered with a removable plastic cover or strip. In some embodiments, when viewed from above as in FIG. 6, the substrate 204 is about 3-6 inches long and about 1-2 inches wide.

Figure 7:
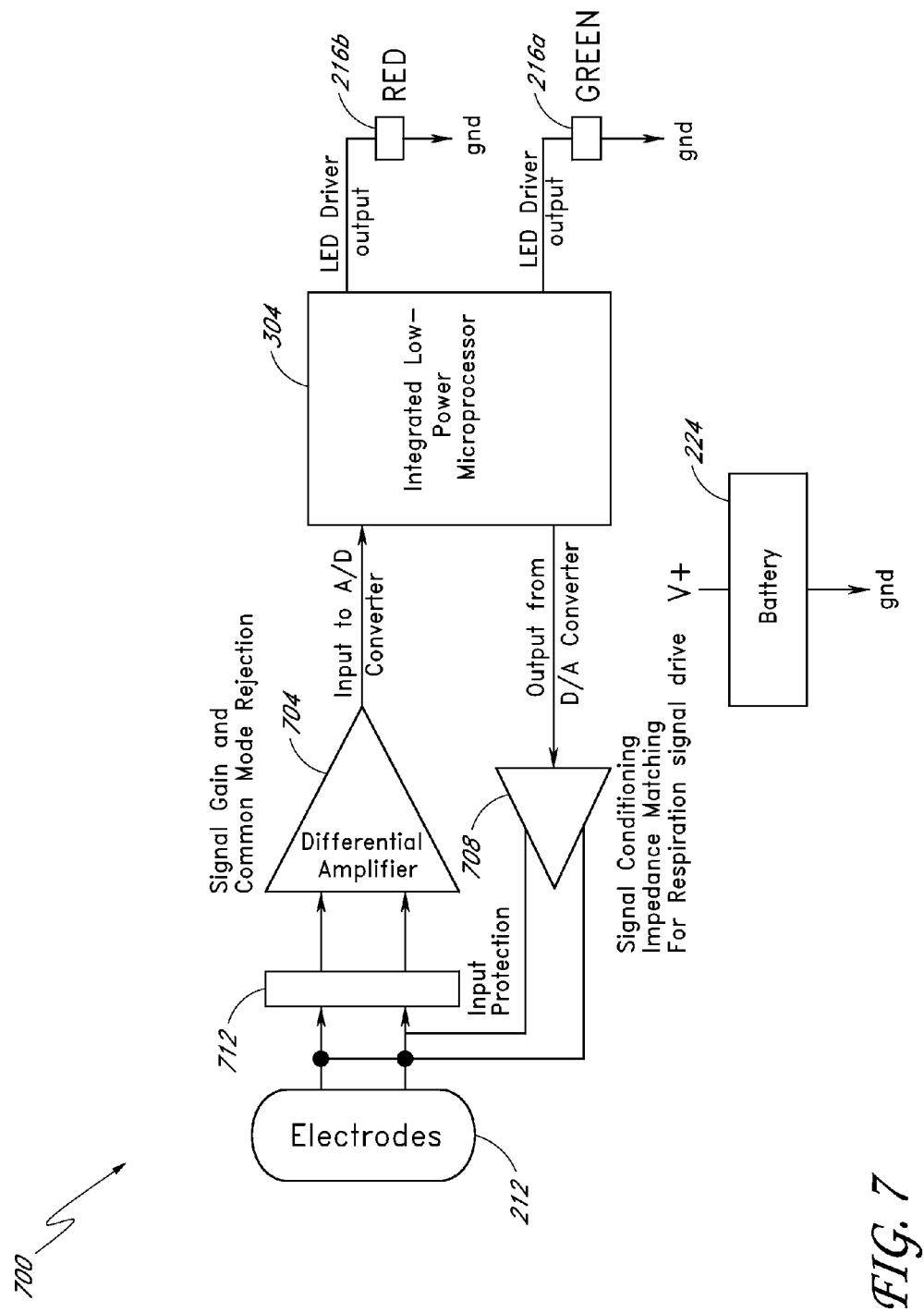
FIG. 7 is a block diagram that schematically illustrates an embodiment of circuitry for a patient status sensor. The circuitry can process body signals to determine heart rate and respiration rate (among other vital signs) and determine patient status based at least in part on the heart rate and respiration rate (or other vital signs).

FIG. 7 is a block diagram of an embodiment of circuitry 700 that can be used with any of the patient status sensors described herein (e.g., the patch sensor 200 or the standalone sensor 600). In various embodiments, many of the components shown in FIG. 7 can be generally similar to the components discussed with reference to FIG. 3. The processor 304 may comprise a single-chip microprocessor such as one from the TI MSP430 family, having integrated analog-to-digital (A/D) and digital-to-analog (D/A) components. In the illustrated embodiment, signals from the electrodes 212 pass through input protection 712 and are amplified by differential amplifier 704 before being digitized by the A/D converter integrated with the processor 304. The digitized signals can be stored in a memory (possibly integrated with the processor 304 or a separate memory in the circuitry 700) as a series of time samples. Two electrode signals are illustrated in FIG. 7, but in other embodiments, a different number of electrode signals can be used (e.g., 1, 3, 4, 5, or more).

In this embodiment, the electrodes 212 and processing circuitry are used for determining heart rate (ECG) and respiration rate. These and/or other vital signs can be determined in other embodiments. In some embodiments, the circuitry 700 can determine the heart rate using the ECG signal from the electrodes 212 using systems and techniques such as, e.g., those described in the chapter "ECG QRS Detection" by Valtino X. Afonso, Chapter 12 in "Biomedical Digital Signal Processing," pp. 236-263, Willis J. Tompkins, editor, Prentice Hall, 1993; the entirety of this chapter is hereby incorporated by reference herein. For example, in some embodiments, digital signal processing techniques can be used to filter the signal from the electrodes 212 to separate the heart signal (ECG signal) from the respiration signal. The ECG signal can be processed to identify the QRS complex (e.g., the R-wave) to determine pulse rate. In some implementations, the signal from the electrodes is bandpass filtered at a center frequency of about 12 Hz to identify the ECG signal. In various embodiments, the bandpass filter can be use a center frequency in a range from about 5 Hz to about 25 Hz.

In certain embodiments, impedance pneumography can be used to determine the respiration rate. In some such embodiments, an alternating current (AC) signal is introduced to the patient's body using the same electrodes 212 utilized for ECG monitoring. In other embodiments, a different set of electrodes is used for the impedance pneumography. As schematically illustrated in FIG. 7, output from the D/A converter (integrated with the processor 304 in this embodiment) is passed through signal conditioning component 708 to provide the AC impedance matching signal for the pneumography. In some implementations, the AC signal can have a current in a range of about several micro-amperes and can be modulated at a frequency at or above about 20 kHz. For example, the AC frequency can be in a range from about 20 kHz to about 50 kHz. Other AC frequencies can be used. The AC signal is introduced to the patient's body (using internal or external analog components) via the electrodes 212 to introduce a voltage to the body surface. The voltage drives a current through the patient's body. Changes in the current or voltage induced by respiratory activity provide an impedance signal that can be measured by the electrodes 212 and used to determine the respiration rate. Changes in impedance can be recognized by changes in the voltage measured by the electrodes 212. For example, respiration can cause an amplitude modulation of the AC carrier signal introduced into the body. Impedance changes can be caused by changes in the body cavity impedance as the patient's lungs are filled and emptied during the respiratory cycle. Signal processing techniques (e.g., filtering) can be used to separate the respiration signal from the heart signal and to separate the modulation caused by respiration from the AC carrier signal.

Various techniques and systems can be used for impedance pneumography including any of those described in, e.g., U.S. Pat. No. 3,677,261 "Impedance Pneumograph", the article "Applications of the Impedance Technique to the Respiratory System," by Lee E. Baker, IEEE Engineering in Medicine and Biology Magazine, March 1989, pp. 50-52, or the article "Critical review of non-invasive respiratory monitoring in medical care," by M. Folke et al., Medical & Biological Engineering & Computing 2003, vol. 41, pp. 377-383. Each of the aforementioned '261 patent, the Baker article, and the Folke et al. article is hereby incorporated by reference herein in its entirety.

Figure 8:
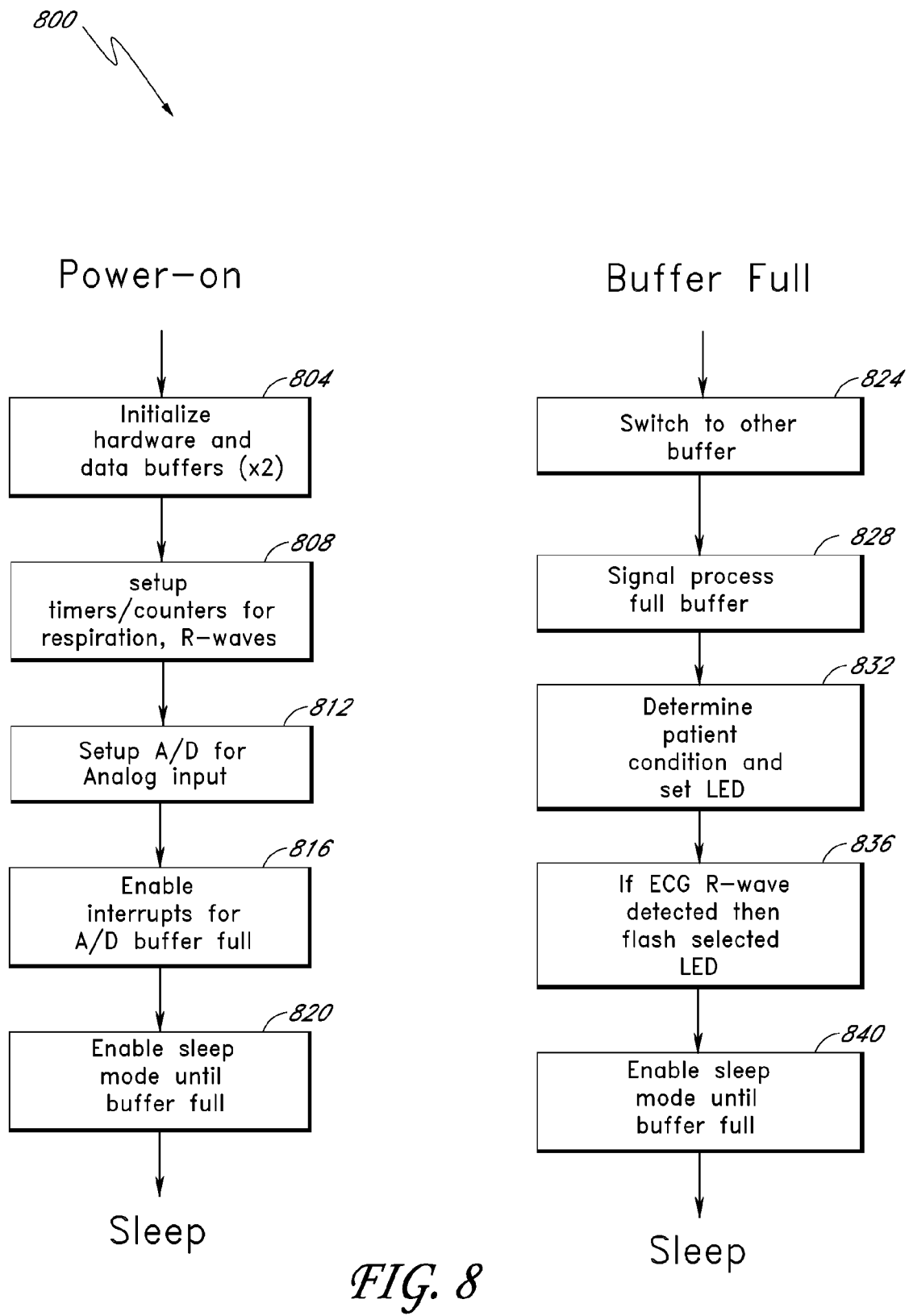
FIG. 8 is a flowchart schematically illustrating an example of a process that can be used by the circuitry of a patient status sensor to provide an indication of patient status.

Accordingly, embodiments of the circuitry 700 can be used to measure a heart signal to determine a heart or pulse rate and measure a respiration signal to determine a respiration rate. The processor 304 can be configured to execute software modules or instructions to determine pulse and respiration rate. For example, FIG. 8 is a flowchart for an embodiment of a process 800 that can be used by the circuitry 700 of a patient status sensor to provide a visual indication of patient status (based at least in part on heart rate and respiration rate). In this embodiment, in block 804 two data buffers are used to store digitized signals from the electrodes 212. In other embodiments, a single buffer or more than two buffers may be used. In block 808, timers and/or counters are initialized for measuring respiration and ECG signals (e.g., an R-wave signal). In block 812, an A/D is initialized for analog input from the electrodes 212, and in block 816 interrupts are enabled to indicate when the first A/D buffer is filled with digitized samples. In block 820, a sleep mode is enabled until the first buffer is full. When the first buffer is full, digitized signals are stored in the second buffer (block 824), and the first (full) buffer is signal processed (block 828) by the processor 304. In block 832, the processor 304 determines patient status and sets one or more of the LEDs 216a, 216b. In other embodiments, audible indicators may (additionally or alternatively) be set by the processor 304. In the illustrated embodiment, the patient status can be based at least in part on a determination of respiration rate and heart rate. In other embodiments, the patient status is based at least in part on additional or alternative vital signs. The processor 304 may determine patient status using an embodiment of the method 1000 described with reference to FIG. 10. In some embodiments, values for respiration rate and heart rate (pulse) can be determined by the processor 304 using an embodiment of the process 900 described with reference to FIG. 9.

Continuing with this illustrative example, in block 836, if a heart beat is measured (e.g., by detecting the R-wave), one of the LEDs 216a, 216b is blinked or flashed. In other embodiments, an audible indicator may be beeped. In block 840, sleep mode is enabled until the second buffer is full, and then the process returns to block 828 to signal process the second buffer. The first buffer can be cleared (or overwritten) to store new digitized samples. The process can repeat while the patient status sensor is attached to the patient and collecting data via the electrodes 212.

Figure 9:
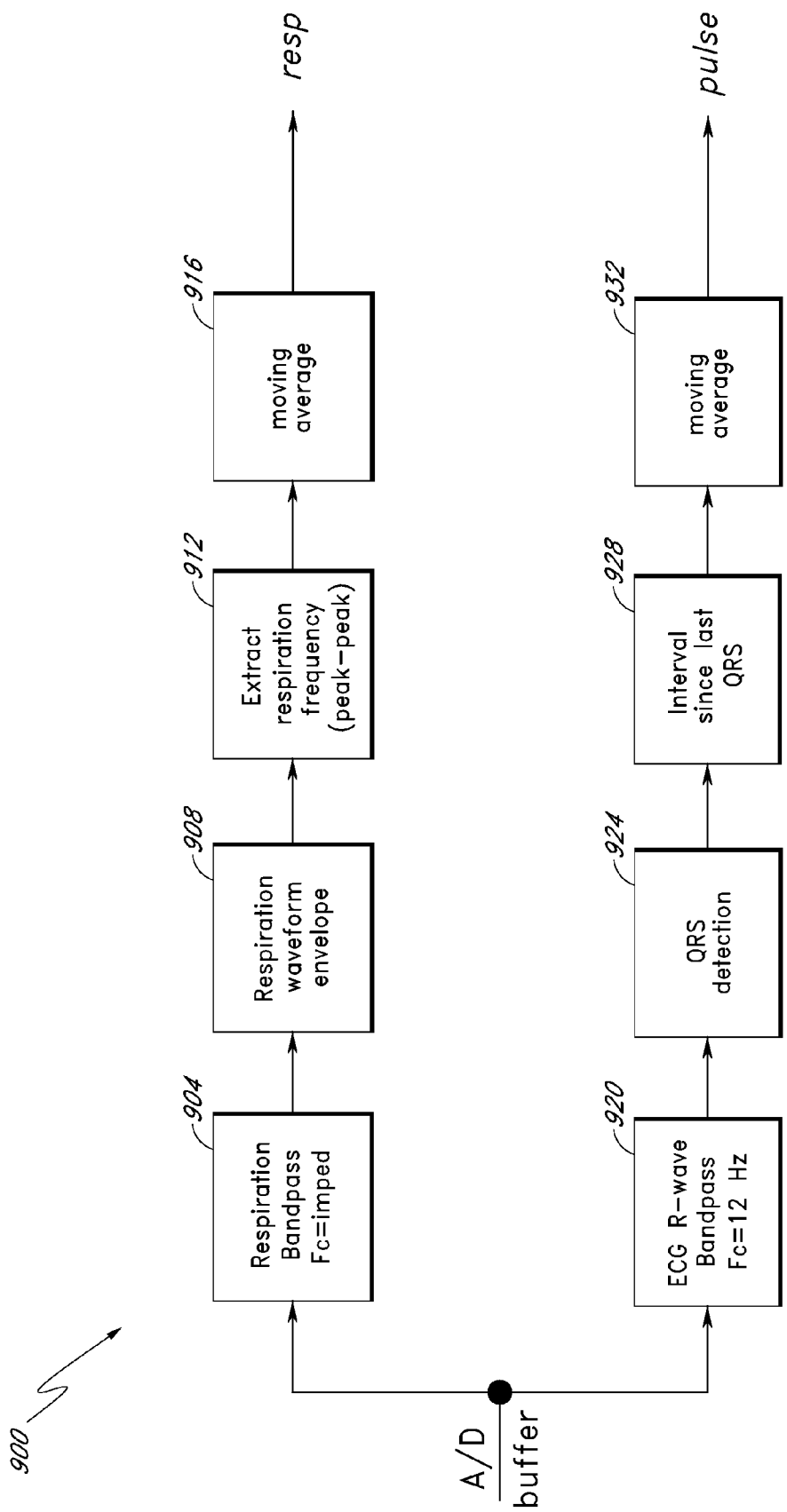
FIG. 9 is a block diagram schematically illustrating an example of a process for determining respiration rate and heart rate (pulse).

FIG. 9 is a block diagram schematically illustrating a process 900 for determining respiration rate (resp) and heart rate (pulse). In this embodiment, digitized signals from the A/D buffer are filtered to determine a respiration signal (block 904) and an ECG signal (block 920). For example, the digitized signal may be bandpass filtered around a central impedance frequency (e.g., above about 20 kHz) to determine the respiration signal and may also be bandpass filtered around central ECG frequency (e.g., about 12 Hz) to determine the ECG signal (e.g., an R-wave signal). The respiration signal and the ECG signal may be further processed either serially or in parallel.

For the respiration signal, in block 908 the envelope of the respiration waveform is determined, and in block 912 the respiration frequency is determined. For example, the respiration frequency may be estimated based on the time separation between successive peaks of the envelope. In the illustrated embodiment, estimates of the respiration frequency are averaged (e.g., using a moving average in some embodiments) to determine a value resp for the respiration rate.

For the ECG signal, in block 924 the QRS complex is detected, and in block 928 a time interval since the last detection of a QRS complex is determined. The time intervals can be averaged (e.g., using a moving average in some embodiments) to determine a value pulse for the heart rate.

Although both respiration rate and heart rate are determined in the method 900 schematically illustrated in FIG. 9, in other embodiments only respiration rate is determined or only heart rate is determined. In yet other embodiments, additional or different vital signs (e.g., temperature, blood pressure, glucose, SpO2) are determined by the patient status sensor.

Figure 10:
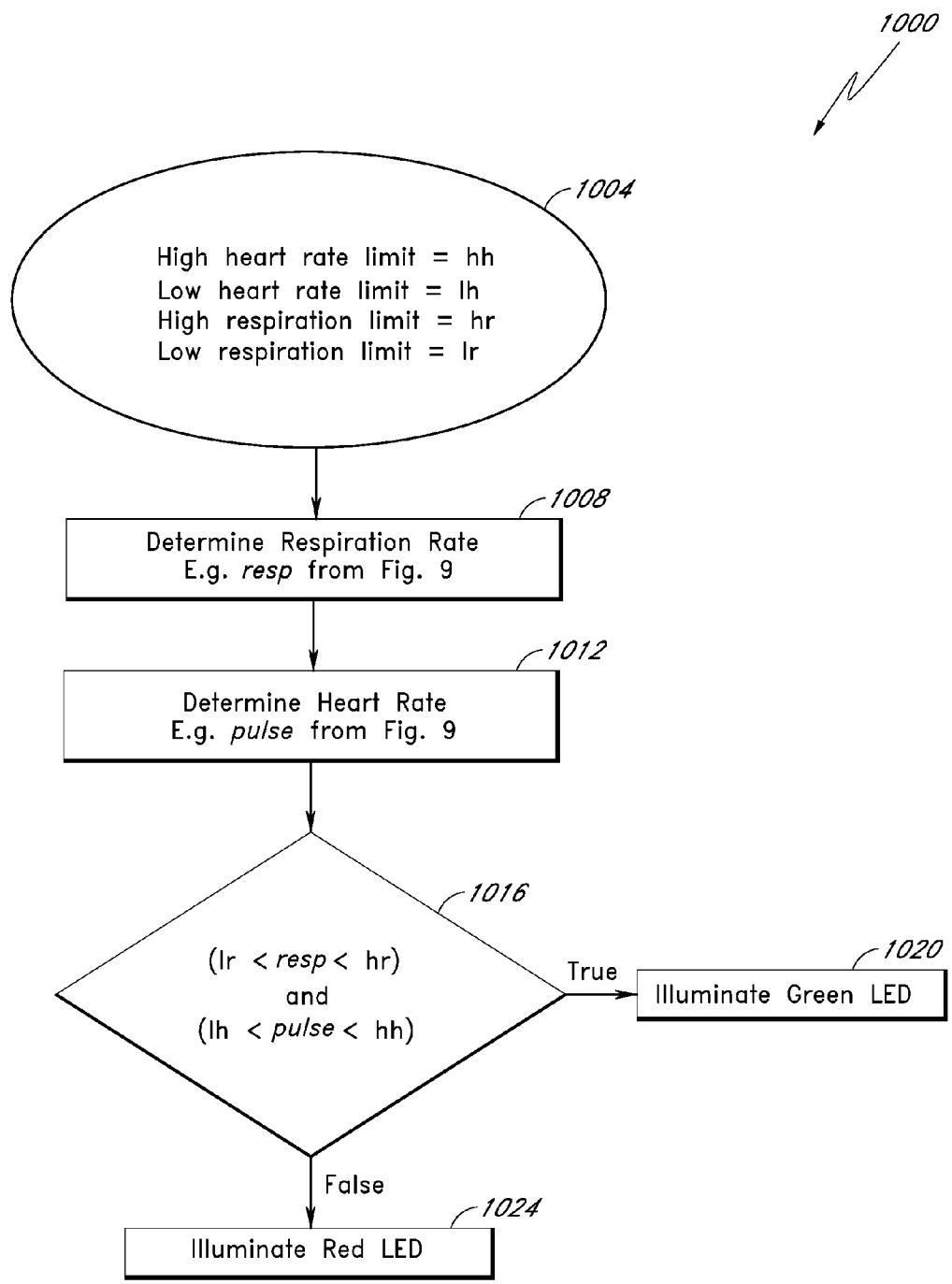
FIG. 10 is a flowchart schematically illustrating an example of a method for determining patient status.

FIG. 10 is a flowchart schematically illustrating a method 1000 for determining patient status. Patient status may be determined using an algorithm based at least in part on one or more measured vital signs and one or more limits, thresholds, or parameters. In some embodiments, the method 1000 can be implemented as software or firmware (e.g., code modules or executable instructions) and executed by the processor 304.

Figures 1, 11:
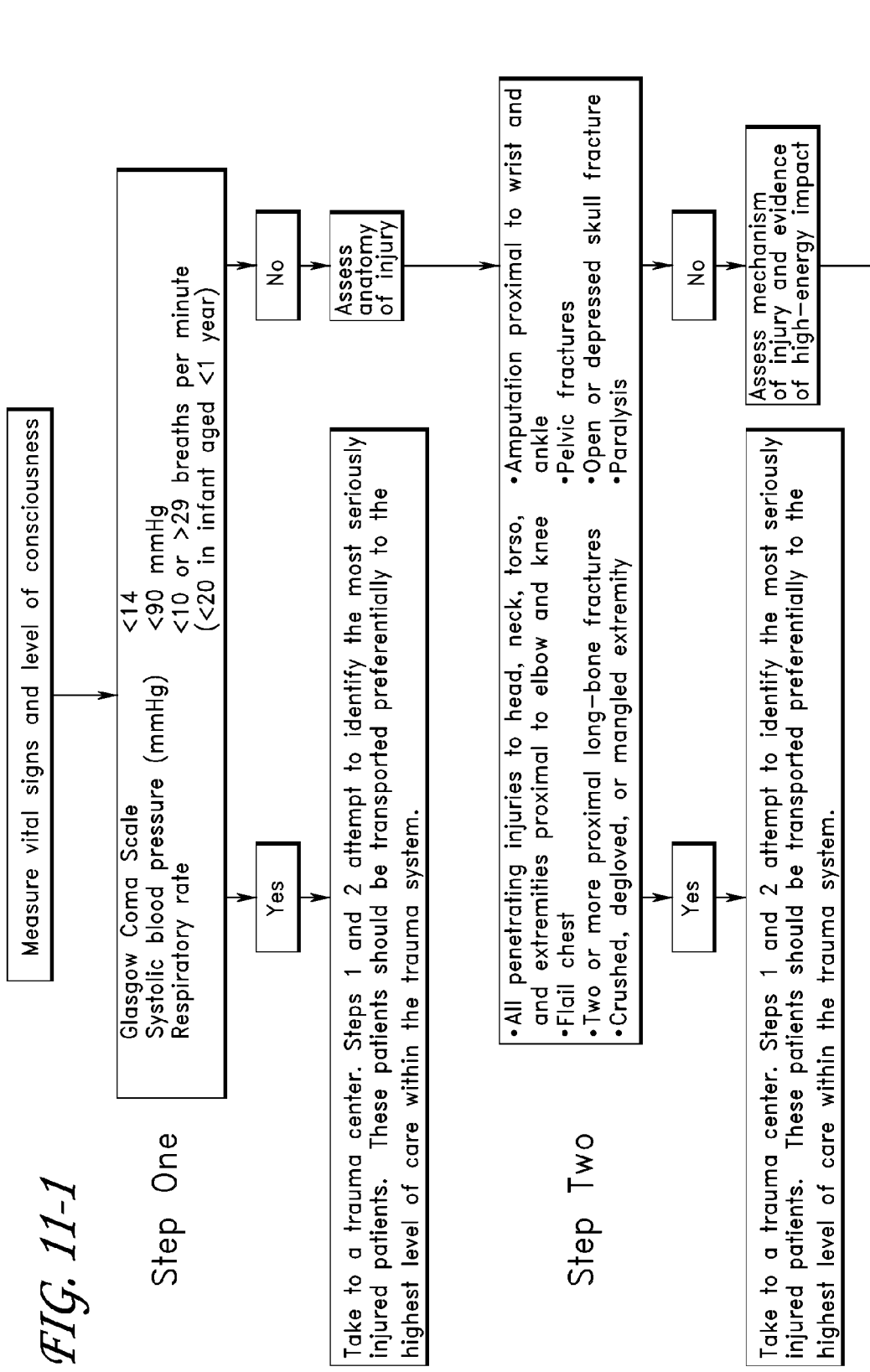
FIG. 11 is a flowchart showing an example of a field triage decision scheme.
Figures 2, 11:
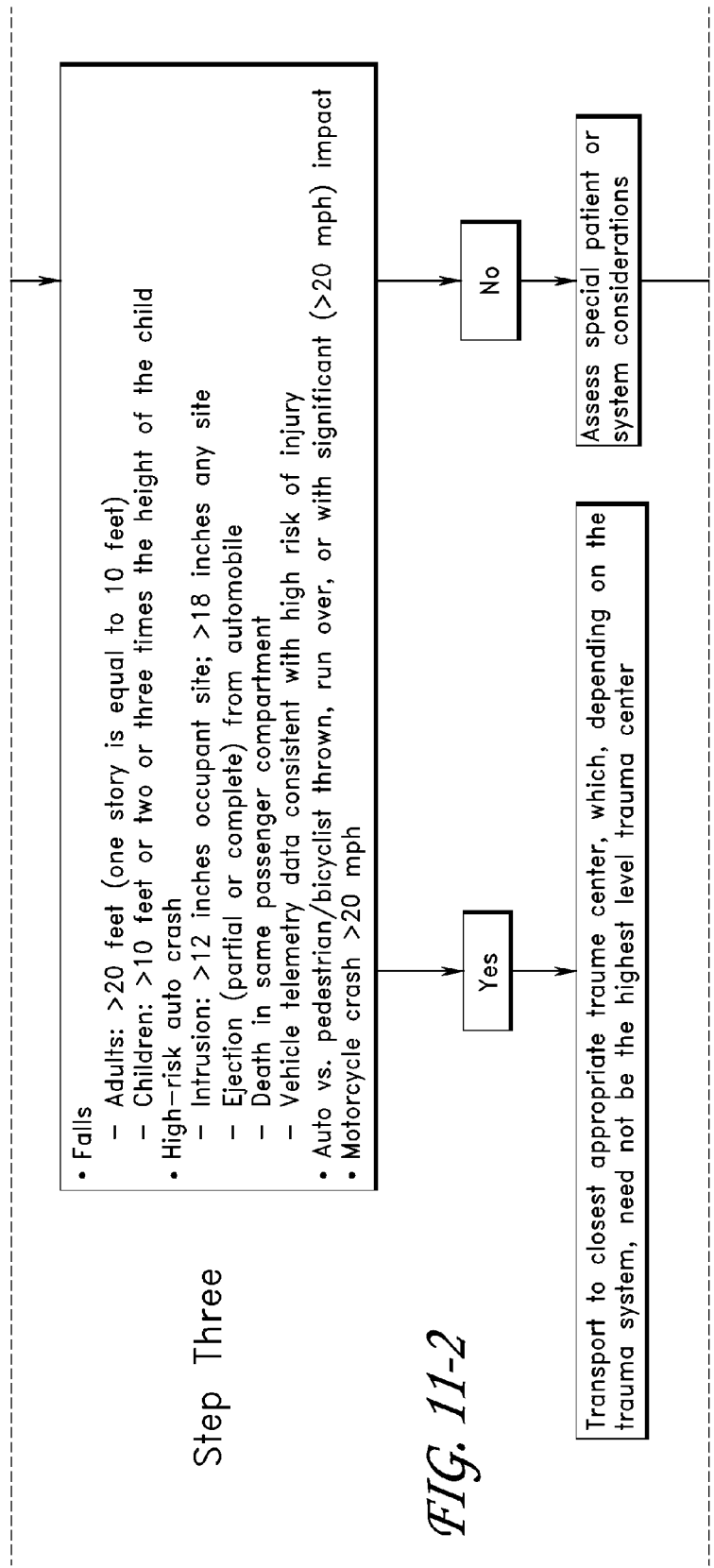
Figures 3, 11:
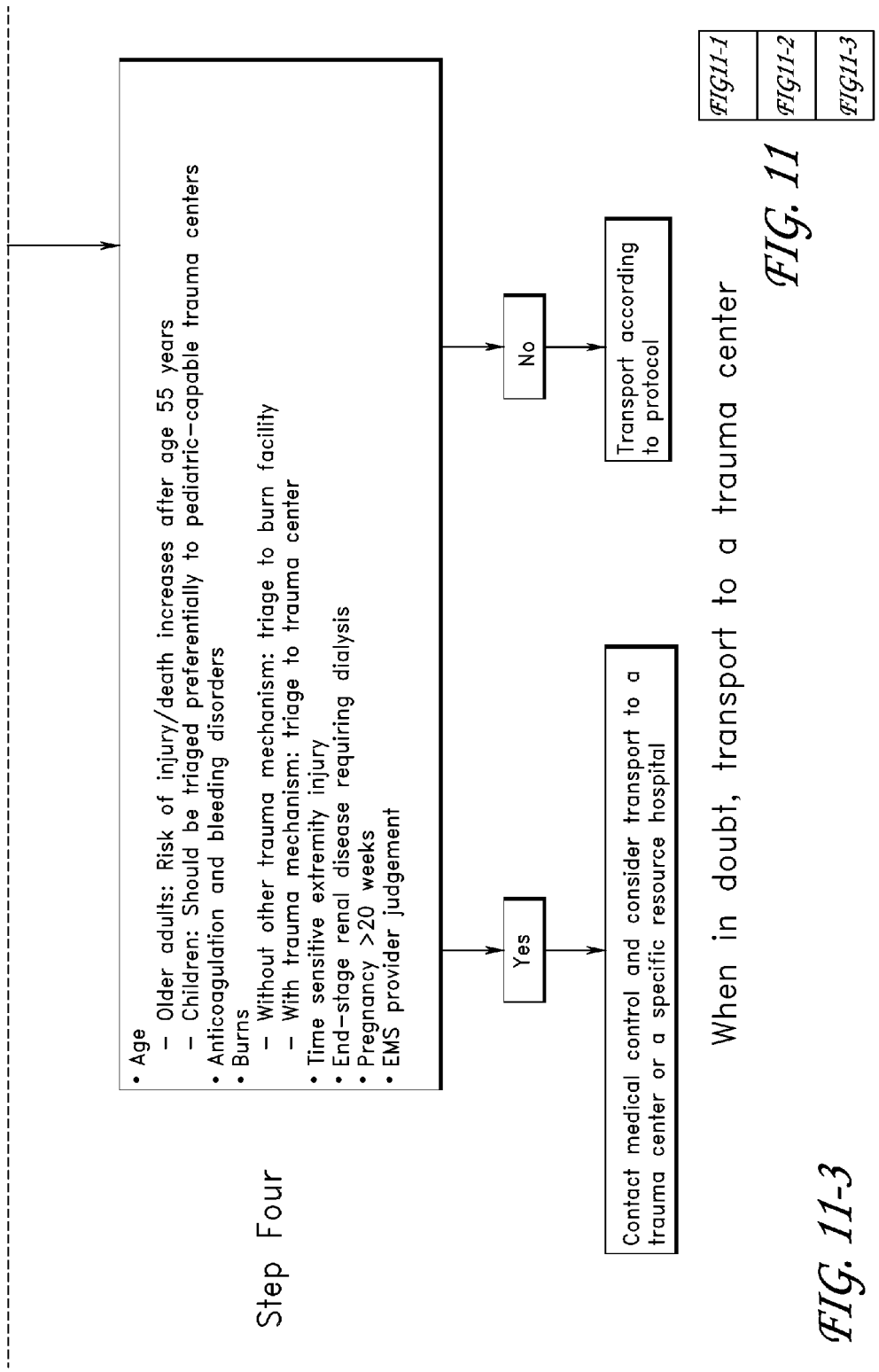

In this example, patient status is based at least in part on one or more vital signs (e.g., heart rate (pulse) and respiration rate (resp)) as well as one or more vital signs limits (for heart rate and respiration rate). The vital signs limits may be selected to reflect ranges for vital signs in which a patient's status is satisfactory (or unsatisfactory) based on medical guidelines, triage decision criteria, or other standards. An example of a field triage decision scheme is illustrated in FIG. 11 and is based on "Guidelines for Field Triage of Injured Patients: Recommendations of the National Expert Panel on Field Triage," Morbidity and Mortality Weekly Report, Centers for Disease Control and Prevention, Jan. 23, 2009, vol. 48, no. RR-1. In some implementations, a patient's status is satisfactory if one or more vital signs are within corresponding vital sign limits and the patient's status is unsatisfactory if one or more vital signs are outside corresponding vital sign limits. The vital signs limits (or any other parameters or factors) can be selected based at least in part on whether the patient status sensor is configured for use on adult patients, child or pediatric patients, infant patients, geriatric patients, ICU patients, battlefield patients, emergency or trauma patients, and so forth. Vital signs limits (or any other parameter or factor) can be selected based at least in part on patient demographics, age, sex, and so forth. Patient status sensors may be labeled to indicate the type of patient the sensor is configured for use with (e.g., labeled for adult use, pediatric use, age ranges, etc.).

In the example schematically illustrated in FIG. 10, in block 1004 high and low limits for heart rate (denoted by hh and lh, respectively) and high and low limits for respiration rate (denoted by hr and lr, respectively) are stored in persistent memory on the patient status sensor. In some implementations, appropriate limits are stored in memory on the sensor (or integrated with the processor) during production of the sensor. For example, if a sensor for adult use is being produced, adult vital signs limits are stored in the memory, etc. In some embodiments, high limits are not used and the low limits reflect minimum values for pulse and respiration. In some implementations, the respiration limits are: lr=10 breaths per minute and hr=29 breaths per minute. Other values can be used. In some implementations, the low limit for heart rate may reflect limits for bradycardia or low heart rate, and the high limit for heart rate may reflect limits for tachycardia or high heart rate. For example, in some implementations, the heart rate limits are: lh=50 beats per minute and hh=100 beats per minute. Other values can be used. Also, in other embodiments, additional or alternative parameterizations, factors, constants, and values may be used in the algorithm or process for determining patient status from vital signs measurements.

Continuing with the example schematically illustrated in FIG. 10, in blocks 1008 and 1012 respiration rate and heart rate are determined, respectively. For example, embodiments of the process 900 described with reference to FIG. 9 may be used to determine resp and pulse. In block 1016, patient status is determined based at least in part on the vital signs (e.g., resp and pulse) and the vital signs limits (e.g., high and low limits for resp and pulse). In this illustrative, non-limiting example, patient status is considered satisfactory if the measured respiration rate is between the low and high respiration limits (lr<resp<hr) and the measured heart rate is between the low and high heart rate limits (lh<pulse<hh). If both parentheticals evaluate to true, patient status is satisfactory and in block 1020 a command is communicated to the LED device driver to illuminate the green LED 216a to signal to medical attendants that the patient's status is satisfactory. If either of the parentheticals evaluate to false, patient status is unsatisfactory and in block 1024 a command is communicated to the LED device driver to illuminate the red LED 216b to signal to medical attendants that the patient's status is unsatisfactory. In various embodiments, if a pulse (or respiration) is detected, the illuminated LED is time modulated (e.g., blinked) at the measured heart rate (or respiration rate). Possible advantages of the example method 1000 are that the patient status algorithm is relatively straightforward to implement in the processor 304 and may lead to fewer false positives (or false negatives). In some embodiments, to reduce false positives (or false negatives), one or more additional vital signs may be included, time delays may be used, or longer term monitoring can be processed via, e.g., averaging or filtering. One or more noise reduction filters can be included to reduce the likelihood that unwanted data from the signal might trigger false readings. In other embodiments, patient status can be determined based at least in part on one or more other vital signs including, e.g., blood pressure, temperature, glucose, SpO2, etc.

Embodiments of the patient status sensor described herein may provide advantages. For example, a medical attendant can determine the patient's vital sign status by simply looking at the visual indicators on the sensor (e.g., to determine the color and the blink rate of the LED) or by listening to the audio indicators, if included (e.g., to determine the sound, tone, or modulation of the audio output). Embodiments of the sensor advantageously may allow the medical attendant to tell "at-a-glance" whether the patient is within medical or triage guidelines or whether the patient requires immediate treatment.

Embodiments of the sensor patch can be used for triage in situations where there are a large number of casualties, and medical attendants need to quickly and reliably determine (e.g., "at-a-glance") which patients need immediate treatment and which patients are stable.

Because some embodiments of the patient sensor do not include wired or wireless components to communicate signals/data "off" the sensor, some such embodiments of the sensor advantageously do not interfere with treatments or complicate movement of the patient (e.g., there are no wires to tangle). The patient status sensor can easily be removed from the patient when no longer needed or when the power source discharges by lifting an edge of the sensor substrate and peeling back the sensor from the patient's skin. Embodiments can be designed as single-use, disposable sensors and provided in sterile packaging. Such embodiments can be safely disposed of after use.

Variations in the methods disclosed herein are possible. For example, additional steps may be included, steps may be removed, steps may be combined, and/or the order of the steps may be altered. Similarly, embodiments of the sensors may be configured differently than shown and described herein. For example, additional components may be added, components may be removed, components may be combined, or the order and/or placement of the components may be altered. The components and the sensors may have different sizes, shapes, and/or features incorporated therein. The components and the sensors may also comprise additional and/or different materials. Still other variations in the arrangement of the components and the sensors and their configuration as well as methods of use of and/or manufacturing are possible.

The various blocks and modules of the methods, processes, and circuits described herein can be particularly implemented as software applications, hardware and/or software programs, or components on one or more processors. The modules may include, but are not limited to, any of the following: software or hardware components such as object-oriented software components, class components and task components, processes, methods, functions, attributes, procedures, subroutines, segments of program code, drivers, firmware, microcode, circuitry, data, databases, data structures, tables, arrays, variables, combinations of the same, and the like. While various modules may be described separately in the foregoing, they may share some or all of the same underlying logic or code.

In addition, each of the methods, processes, blocks, and algorithms described herein may be particularly embodied in, and fully or partially automated by, modules executed by one or more computers or computer processors. The processes and algorithms may also be particularly implemented partially or wholly in application-specific circuitry. For example, in some embodiments, a field-programmable gate array (FPGA), an application-specific integrated circuit (ASIC), and/or a programmable logic device (PLD) may be particularly configured to perform one or more blocks or modules of the disclosed methods and systems. In some embodiments, a general purpose computer (or processor) may be particularly configured to emulate, partially or wholly, such application-specific circuitry.

Some or all of the computers or computer processors may be configured to communicate over a wired or wireless network, such as, e.g., a wide-area network, a local-area network, or the Internet. The modules may be stored on any type of computer-readable medium or computer storage device (including volatile or non-volatile memory) such as, for example, magnetic storage (e.g., hard disk drives), semiconductor storage (e.g., RAM, ROM, EEPROM, or flash memory), or optical storage (e.g., CD-ROM or DVD). The computer-readable medium may be non-transitory. The results of the disclosed processes and process steps (and/or any information relating thereto) may be stored, persistently or otherwise, in any type of computer storage. Some embodiments include a computer-readable medium having stored thereon a set of program modules that, when executed by a processor, cause the processor to particularly perform an embodiment of the disclosed methods and processes. The computer-readable medium may comprise a non-transitory storage medium.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Accordingly, while the above detailed description has shown, described, and pointed out novel features as applied to various embodiments, it will be understood that various omissions, substitutions, and changes in the form and details of the device or process illustrated may be made by those skilled in the art. No single feature or process step, or group of features or process steps, is required or indispensable for any particular embodiment. Thus, for example, it should be recognized that the various embodiments may be carried out in a manner that achieves or optimizes one advantage or group of advantages as taught herein without necessarily achieving other aspects or advantages as may be taught or suggested herein. As will be recognized, embodiments may be carried out within a form that does not provide all of the features and benefits set forth herein, as some features may be used or practiced separately from others. The various features and processes described above may be used independently of one another, or may be combined in various ways. All possible combinations and subcombinations are intended to fall within the scope of this disclosure. Accordingly, the foregoing description is to be understood as being a broad, teaching disclosure directed to persons of skill in the appropriate arts and not as limiting upon embodiments of the invention.

What is claimed is:

1. An intraosseous (IO) fluid delivery and patient status system, the IO system comprising:
   an IO infusion device configured to provide access to an IO space in a bone of a patient, the IO infusion device comprising:
      a bone portal comprising a fluid delivery channel, the bone portal having a proximal end and a distal end, the distal end configured to be inserted into the bone; and
      a fluid delivery conduit configured to be coupled to the proximal end of the bone portal so as to provide fluid access to the fluid delivery channel of the bone portal; and
   a patient status sensor configured to monitor at least heart rate and respiration rate of the patient, the patient status sensor comprising:
      a substrate comprising an adhesive component configured to adhere the patient status sensor to the patient;
      a pair of electrodes disposed in or on the substrate the pair of electrodes configured to receive an electrical signal from the body of the patient and in response to provide a body signal comprising a single-channel electrocardiogram (ECG) signal;
      a visual indicator;
      a processor configured to (a) receive and process the body signal from the pair of electrodes in order to determine measurements of heart rate and respiration rate, the heart rate determined from the single-channel ECG signal, (b) determine patient status based at least in part on: (b1) the measurement of the heart rate and one or more heart rate limits and (b2) the measurement of the respiration rate and one or more respiration rate limits, and (c) output a patient status signal to the visual indicator, the visual indicator configured to output visual information indicative of the patient status; and
      a power source configured to be electrically connected to the visual indicator and the processor.

2. The IO system of claim 1, wherein the distal end of the bone portal is configured to be inserted into the sternum of the patient.

3. The IO system of claim 1, wherein the electrodes of the pair of electrodes are disposed in or on the adhesive component.

4. The IO system of claim 1, wherein the visual indicator, the processor, and the power source are disposed in or on the substrate.

5. The IO system of claim 1, wherein the visual indicator comprises one or more light emitting diodes.

6. The IO system of claim 5, wherein at least one of the one or more light emitting diodes is configured to output a time-varying visual signal, the time-varying visual signal indicative of a time-variation of the body signal.

7. The IO system of claim 6, wherein the time-varying visual signal comprises blinking or flashing, and the time-variation of the body signal comprises heartbeat or respiration.

8. The IO system of claim 1, wherein the power source comprises a battery.

9. The IO system of claim 1, further comprising a removable pull tab configured to electrically isolate the power source from the visual indicator and the processor and to electrically connect the power source to the visual indicator and the processor when the pull tab is removed.

10. The IO system of claim 9, further comprising a package configured to store the IO system, the package and the pull tab configured such that the pull tab is automatically removed when the package is opened by a user.

11. The IO system of claim 1, wherein the one or more heart rate limits comprise a heart rate lower limit and a heart rate upper limit, the one or more respiration rate limits comprise a respiration rate lower limit and a respiration rate upper limit and the processor is configured to determine patient status based at least in part on one or both of: whether the measurement of the heart rate is between the heart rate lower limit and the heart rate upper limit; and whether the respiration rate is between the respiration rate lower limit and the respiration rate upper limit.

12. The IO system of claim 11, wherein the visual indicator comprises a first light source and a second light source, and the processor is configured to illuminate the first light source if the measurement of the heart rate or breathing rate is between the lower limit and the upper limit and to illuminate the second light source if the measurement of the heart rate or breathing rate is not between the lower limit and the upper limit.

13. The IO system of claim 1, further comprising an audible indicator, the processor configured output a second patient status signal to the audible indicator.

14. The IO system of claim 1, wherein the patient status sensor is configured to output an impedance signal via the pair of electrodes, and the electrical signal received by the pair of electrodes comprises a modulation of the impedance signal and the processor is configured to measure the respiration rate based at least in part on the modulation of the impedance signal.

15. The IO system of claim 1, further comprising an analyte sensor disposed in or on the bone portal.

16. The IO system of claim 15, wherein the analyte sensor is disposed on an inner surface of the fluid delivery channel of the bone portal.

17. The IO system of claim 15, wherein the analyte sensor comprises at least one of a pressure sensor, a temperature sensor, a blood oxygen sensor, a pH sensor, or a glucose sensor.

18. The IO system of claim 15, wherein the processor is further configured to receive a signal from the analyte sensor and determine a measurement of an additional vital sign based at least in part on the signal from the analyte sensor.

19. The IO system of claim 18, wherein the processor is further configured to determine the patient status based at least in part on the measurement of the additional vital sign.

20. The IO system of claim 1, further comprising a wired or wireless transmission system configured to communicate information related to the measurement of the one or more of the heart rate, the breathing rate and the patient status to an external device.

21. The IO system of claim 20, wherein the transmission system is configured to communicate a frequency modulated or amplitude modulated audio signal.

22. The IO system of claim 20, wherein the transmission system is configured to communicate a radio frequency signal.

23. A patient status sensor configured to monitor at least heart beat and respiration of a patient, the patient status sensor comprising:
   a substrate comprising an adhesive layer configured to adhere the patient status sensor to the patient;
   a visual indicator disposed in or on the substrate;
   a pair of electrodes disposed in or on the substrate, the patient status sensor configured to output an impedance signal via the pair of electrodes to the body of the patient, the pair of electrodes configured to receive from the body of the patient an electrical signal comprising a single-channel electrocardiogram (ECG) signal and a modulation of the impedance signal;
   a processor disposed in or on the substrate, the processor configured to:
      receive and process the electrical signal from the pair of electrodes to determine a measurement of heart rate from the single-channel ECG signal and respiration rate from the modulation of the impedance signal;
      determine patient status based at least in part on (a) the measurement of the heart rate and one or more heart rate limits and (b) the measurement of the respiration rate and one or more respiration rate limits; and
      output a patient status signal to the visual indicator in response to the determination of the patient status, the visual indicator configured to output visual information indicative of at least one of the heart rate, the respiration rate, and the patient status; and
   a power source disposed in or on the substrate, the power source configured to be electrically connected to the plurality of electrodes, the visual indicator, and the processor.

24. The patient status sensor of claim 23, wherein the visual indicator comprises one or more light emitting diodes.

25. The patient status sensor of claim 24, wherein at least one of the one or more light emitting diodes is configured to output a time-varying visual signal, the time-varying visual signal indicative of the measurement of the heart rate or the measurement of the respiration rate.

26. The patient status sensor of claim 25, wherein the time-varying visual signal comprises blinking or flashing.

27. The patient status sensor of claim 23, wherein the power source comprises a battery.

28. The patient status sensor of claim 23, further comprising a removable pull tab configured to electrically isolate the power source from the plurality of electrodes, the visual indicator, and the processor and to electrically connect the power source to the plurality of electrodes, the visual indicator, and the processor when the pull tab is removed.

29. The patient status sensor of claim 28, further comprising a package configured to store the patient status sensor, the package and the pull tab configured such that the pull tab is automatically removed when the package is opened by a user.

30. The patient status sensor of claim 23, wherein the one or more heart rate limits comprise a lower heart rate limit and an upper heart rate limit, the one or more respiration rate limits comprise a lower respiration rate limit and an upper respiration rate limit, and the processor is configured to determine patient status based at least in part on whether the measurement of the heart rate is between the lower heart rate limit and the upper heart rate limit and whether the measurement of the respiration rate is between the lower respiration rate limit and the upper respiration rate limit.

31. The patient status sensor of claim 23, wherein the visual indicator comprises a first light source and a second light source, and the processor is configured to illuminate the first light source if the patient status is satisfactory and to illuminate the second light source if the patient status is unsatisfactory.

32. The patient status sensor of claim 23, wherein the processor is configured to illuminate the visual indicator only if there is a change in the patient status.

33. The patient status sensor of claim 23, further comprising an audible indicator, the processor configured output a second patient status signal to the audible indicator.

34. The patient status sensor of claim 23, wherein the impedance signal comprises an alternating current having a frequency greater than about 20 kHz.

35. The patient status sensor of claim 23, wherein the processor is configured to process the electrical signal to separate the ECG signal and the respiration signal from the electrical signal.

36. The patient status sensor of claim 35, wherein the processor is configured to filter the electrical signal with a bandpass at a central ECG frequency to separate the ECG signal and to filter the electrical signal with a bandpass at a central respiration frequency to separate the respiration signal.

37. The patient status sensor of claim 36, wherein the central ECG frequency is about 12 Hz and the central respiration frequency is above about 20 kHz.

38. The patient status sensor of claim 23, wherein the substrate comprises an access opening configured to receive an intraosseous needle assembly for intraosseous delivery of a fluid to bone marrow.

39. The patient status sensor of claim 38, wherein the substrate includes at least one marker for locating the substrate on an anatomical location on the body of the patient.

40. The patient status sensor of claim 39, wherein the anatomical location comprises a location on the sternum of the patient.

* * * * *